US011347147B2

(12) United States Patent
Naito et al.

(10) Patent No.: US 11,347,147 B2
(45) Date of Patent: May 31, 2022

(54) METAL-CONTAINING ONIUM SALT COMPOUND, PHOTODEGRADABLE BASE, RESIST COMPOSITION, AND METHOD FOR MANUFACTURING DEVICE USING SAID RESIST COMPOSITION

(71) Applicant: TOYO GOSEI CO., LTD., Chiba (JP)

(72) Inventors: Michiya Naito, Chiba (JP); Masamichi Hayakawa, Chiba (JP); Yoshiyuki Utsumi, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 317 days.

(21) Appl. No.: 16/344,093

(22) PCT Filed: Oct. 25, 2017

(86) PCT No.: PCT/JP2017/038522
§ 371 (c)(1),
(2) Date: Apr. 23, 2019

(87) PCT Pub. No.: WO2018/084050
PCT Pub. Date: May 11, 2018

(65) Prior Publication Data
US 2019/0243243 A1 Aug. 8, 2019

(30) Foreign Application Priority Data

Nov. 7, 2016 (JP) .............................. JP2016-216979

(51) Int. Cl.
| | | |
|---|---|---|
| *G03F 7/039* | (2006.01) | |
| *G03F 7/30* | (2006.01) | |
| *G03F 7/38* | (2006.01) | |
| *C07C 381/12* | (2006.01) | |
| *C07F 7/22* | (2006.01) | |
| *G03F 7/004* | (2006.01) | |
| *G03F 7/20* | (2006.01) | |
| *G03F 7/038* | (2006.01) | |
| *C07C 309/19* | (2006.01) | |
| *C07C 309/12* | (2006.01) | |
| *C07C 309/06* | (2006.01) | |

(52) U.S. Cl.
CPC ............ *G03F 7/039* (2013.01); *C07C 309/06* (2013.01); *C07C 309/12* (2013.01); *C07C 309/19* (2013.01); *C07C 381/12* (2013.01); *C07F 7/22* (2013.01); *C07F 7/2208* (2013.01); *G03F 7/004* (2013.01); *G03F 7/0042* (2013.01); *G03F 7/0045* (2013.01); *G03F 7/038* (2013.01); *G03F 7/20* (2013.01); *G03F 7/30* (2013.01); *C07C 2602/42* (2017.05); *C07C 2603/74* (2017.05); *G03F 7/38* (2013.01); *Y02P 20/55* (2015.11)

(58) Field of Classification Search
CPC ........ G03F 7/0045; G03F 7/038; G03F 7/039; G03F 7/30; G03F 7/38
See application file for complete search history.

(56) References Cited

U.S. PATENT DOCUMENTS

| | | |
|---|---|---|
| 2009/0234155 A1 | 9/2009 | Oh et al. |
| 2011/0015431 A1 | 1/2011 | Jodry et al. |
| 2011/0034721 A1 | 2/2011 | Hagiwara et al. |
| 2011/0319652 A1 | 12/2011 | Jodry et al. |
| 2012/0289738 A1 | 11/2012 | Hosoi et al. |
| 2013/0317250 A1 | 11/2013 | Hagiwara et al. |
| 2017/0174711 A1* | 6/2017 | Miyazawa ............ C08G 65/18 |

FOREIGN PATENT DOCUMENTS

| | | |
|---|---|---|
| JP | 2004-191764 A | 7/2004 |
| JP | 2009-091351 A | 4/2009 |
| JP | 2009-221454 A | 10/2009 |
| JP | 2010-066492 A | 3/2010 |
| WO | 2011/093139 A1 | 8/2011 |

OTHER PUBLICATIONS

Translation of International Search Report dated May 11, 2018 in corresponding International application No. PCT/JP2017/038522; 2 pages.

Kitamura, et al., "Reaction of (diacetoxyiodo)benzene with excess of trifluoromethanesulfonic acid. A convenient route to paraphenylene type hypervalent iodine oligomers", Tetrahedron, 2004, 60 (40), pp. 8855-8860; 6 pages.

Bravo, et al., "Computational Insight into the Reaction Intermediates in the Glycosylation Reaction Assisted by Donor Heteroatoms", Journal of Organic Chemistry, 2003, 68 (3), pp. 686-691; 6 pages.

* cited by examiner

*Primary Examiner* — John S Chu
(74) *Attorney, Agent, or Firm* — Maier & Maier, PLLC

(57) ABSTRACT

A metal-containing onium salt compound suitable for use as a photodegradable base of a resist composition and a resist composition using the metal-containing onium salt compound are provided, the resist composition having excellent sensitivity to ionizing radiation such as extreme ultraviolet (EUV), excellent resolution and focal depth in lithography, and can reduce line width roughness (LWR) in a fine pattern. The onium salt compound including a specific metal is used as the photodegradable base.

10 Claims, No Drawings

METAL-CONTAINING ONIUM SALT COMPOUND, PHOTODEGRADABLE BASE, RESIST COMPOSITION, AND METHOD FOR MANUFACTURING DEVICE USING SAID RESIST COMPOSITION

TECHNICAL FIELD

Several embodiments of the present invention relate to a metal-containing onium salt compound, and more particularly to a metal-containing onium salt compound suitably used for a resist composition for lithography using ionizing radiation such as extreme ultraviolet or the like as an exposure source. Some embodiments of the present invention relate to a degradable base and a resist composition containing the metal-containing onium salt compound, and a method for manufacturing a device using the resist composition.

BACKGROUND

In recent years, manufacturing of display devices such as a liquid crystal display (LCD), an organic EL display (OLED) and the like, and formation of semiconductor elements have been actively performed by a photolithography technology using a photoresist. As an active energy ray, light such as i-line having a wavelength of 365 nm, and h-line of 405 nm, g-line of 436 nm, and the like having a longer wavelength than the i-line are widely used for packages and the like of the above-mentioned electronic components, electronic products.

Since demands for miniaturization of lithography technology has increased as device integration has advanced, light having a very short wavelength such as KrF excimer laser, wavelength of 248 nm, ArF excimer laser, wavelength of 193 nm, extreme ultraviolet (EUV), wavelength of 13.5 nm, and electron beam (EB) tends to be used for exposure. A lithography technology using the short wavelength light, especially ionizing radiation such as extreme ultraviolet (EUV) and the like allows manufacturing using single patterning. Therefore, it is considered that needs for a resist composition having high sensitivity to the ionizing radiation such as the extreme ultraviolet (EUV) and the like further increase in the future.

Along with the shortening of the wavelength of the exposure light source, improvement of lithography performance having sensitivity to the exposure light source and resolution capable of reproducible formation of fine size pattern is required for the resist composition. As the resist composition satisfying such requirements, a chemically amplified resist using an acid generator is known.

However, along with the rapid miniaturization progresses, the chemically amplified resist using the acid generator has a problem that an acid generated by the exposure diffuses in the resist to affect the lithography performance greatly, and resulting that a contrast and line edge roughness (LER) properties of a line pattern are deteriorate. Accordingly, it has been proposed to increase the resolution by incorporating an acid diffusion control agent into the resist composition for a purpose of appropriately controlling the diffusion of the acid generated from the acid generator (Patent Literature 1). On the other hand, when acid diffusivity is excessively suppressed, the contrast may decrease by restriction of chemical reaction by the acid. For this reason, it has been proposed to improve the contrast by using a photodegradable base which is degraded by the exposure to lose acid diffusion controllability (Patent Literature 2).

PRIOR ART LITERATURE

Patent Literature

Patent Literature 1: JP2004-191764A
Patent Literature 2: JP2010-066492A

SUMMARY OF THE INVENTION

Technical Problem

However, since the chemically amplified resist composition for the ionizing radiation such as conventional extreme ultraviolet (EUV) and the like has a low absorption of the ionizing radiation such as EUV and the like, it is difficult to simultaneously satisfy the characteristics of the sensitivity to the ionizing radiation such as EUV and the like, resolution, focal depth and pattern performance. In the acid diffusion control agent proposed in Patent Literature 2, the absorption of the electron beam or EUV is low, and problems remain in terms of the sensitivity to the ionizing radiation such as EUV and the like, resolution, and pattern performance.

Some embodiments of the present invention aim to provide an onium salt compound used in a resist composition having a high absorption efficiency of the ionizing radiation such as EUV and the like, and having excellent characteristics of the sensitivity, resolution and pattern performance.

In addition, some embodiments of the present invention aim to provide a photodegradable base containing the onium salt compound, a resist composition containing the photodegradable base, and a method for manufacturing a device using the resist composition.

Solution to Problem

As a result of diligent studies to solve the above problems, it is found that incorporating a specific onium salt compound as a photodegradable base into a resist composition can improve the absorption efficiency of the ionizing radiation such as EUV and the like, the characteristics of the sensitivity, resolution and pattern performance, and thereby some embodiments of the present invention are completed.

That is, one embodiment of the present invention is a metal-containing onium salt compound represented by the following Formula (1).

$$(R^1)_3\text{-}M\text{-}Ar^1\text{---}Y^+\text{-}(R^2)_n X^- \quad (1)$$

In the above Formula (1), $R^1$ and $R^2$ are each independently an alkyl group having 1 to 20 carbon atoms or an aryl group having 5 to 20 carbon atoms, and a part or all of hydrogen atoms of the alkyl group and the aryl group may be substituted.

$Ar^1$ is an arylene group having 5 to 20 carbon atoms, and a part or all of hydrogen atoms of the arylene group may be substituted.

The alkyl group may contain a hetero atom-containing group instead of at least one methylene group thereof. The aryl group and the arylene group may contain a hetero atom instead of at least one carbon atom in ring structure thereof.

M is any one selected from the group consisting of Ge, Sn and Pb.

Y is any one selected from the group consisting of an iodine atom, a sulfur atom, a selenium atom and a tellurium atom. When Y is the iodine atom, n is 1, and when Y is any one selected from the group consisting of the sulfur atom, the selenium atom and the tellurium atom, n is 2.

Any two or more of $Ar^1$ and two $R^2$ may be bonded to each other to form a ring structure with Y bonded thereto, and the ring structure may contain a hetero atom.

$X^-$ is an anion.

Another embodiment of the present invention is a photodegradable base and a resist composition containing the metal-containing onium salt compound.

Still another embodiment of the present invention is a method for manufacturing a device including: forming a resist film on a substrate using the resist composition; exposing the resist film; and obtaining a resist pattern by developing an exposed resist film.

Effect of the Invention

By containing a specific metal, the metal-containing onium salt compound according to one embodiment of the present invention increases a film absorption of the ionizing radiation such as the extreme ultraviolet (EUV) and the like, efficiency of the ionization and secondary electron generation efficiency, resulting excellence in the sensitivity, resolution and pattern performance.

DETAILED DESCRIPTION OF THE INVENTION

Hereinafter, some embodiments of the present invention will be described in detail.

<1> Metal-Containing Onium Salt Compound

A metal-containing onium salt compound of one embodiment of the present invention has the above-mentioned structure. The above Formula (1) has one -M-$R^3$ group but may have some -M-$R^3$ groups as substituents.

Further, a cation of the metal-containing onium salt compound represented by the above Formula (1) indicates a monocation, but it may be a polycation. When the cation is the polycation, an anion is one corresponding to the polycation.

By containing the specific metal, the metal-containing onium salt compound increases a film absorption of ionizing radiation such as EUV and the like, the ionization efficiency and a secondary electron generation efficiency, resulting that a resist composition containing the metal-containing onium salt compound would be highly sensitive.

By containing the specific metal atom, the metal-containing onium salt compound increases the film absorption of ionizing radiation such as EUV and the like, and the generation efficiency of the secondary electron, resulting that degradation efficiencies of the metal-containing onium salt compound and a photoacid generator are improved. When the metal-containing onium salt compound is a salt having a conjugate base weaker than that of the photoacid generator, an acid generated from the photoacid generator in an unexposed portion can be inactivated by reacting the acid generated from the photoacid generator with the metal-containing onium salt compound, resulting that the metal-containing onium salt compound acts as an acid diffusion control agent. Also, when the metal-containing onium salt compound is a salt having a conjugate base equivalent to that of the photoacid generator, the specific metal existing in the cation in the unexposed portion can inactivate the acid generated from the photoacid generator, resulting that the metal-containing onium salt compound acts as the acid diffusion control agent. Therefore, when the metal-containing onium salt compound of one embodiment of the present invention is used in a resist composition, the resist composition can be excellence in characteristics of the sensitivity, resolution and pattern forming ability.

Some embodiments of the present invention will be specifically described below, but the present invention is not limited thereto.

<1-1> Cation of Metal-Containing Onium Salt Compound

The cation of the metal-containing onium salt compound in one embodiment of the present invention is represented below.

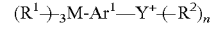

In the above, $R^1$ and $R^2$ are each independently an alkyl group having 1 to 20 carbon atoms or an aryl group having 5 to 20 carbon atoms, and a part or all of hydrogen atoms of the alkyl group and the aryl group may be substituted.

The alkyl group having 1 to 20 carbon atoms includes: a linear alkyl group such as a methyl group, an ethyl group, an n-propyl group, an n-butyl group, an n-pentyl group, an n-hexyl group, an n-octyl group, an n-dodecyl group and the like; a branched alkyl group such as an isopropyl group, an isobutyl group, a tert-butyl group, an isopentyl group, a tert-pentyl group, a 2-ethyloctyl group, a 2-ethyldecyl group and the like; an alicyclic alkyl group such as a cyclopropyl group, a cyclobutyl group, a cyclopentyl group, a cyclohexyl group, a cyclooctyl group, a decahydronaphthyl group and the like; and the like.

Other examples of the alicyclic alkyl group include: a spiro alicyclic alkyl group such as a spiro [3,4] octyl group, a spirobicyclopentyl group and the like; a bridged alicyclic alkyl group such as a norbornyl group, a tricyclodecanyl group, a tetracyclododecanyl group, an adamantyl group and the like; and a condensed-ring alicyclic alkyl group such as a decalin and a group having a steroid skeleton represented below and the like; and the like.

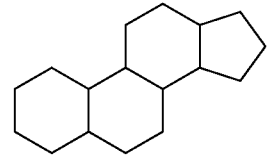 [SMILES: C1CCC2C(C1)CCC1C3CCCC3CCC21]

Also, instead of at least one methylene group in these alkyl groups, a divalent hetero atom-containing group may be contained. The hetero atom-containing group is at least one selected from the group consisting of —O—, —CO—, —COO—, —OCO—, —O—CO—O—, —NHCO—, —CONH—, —NH—CO—O—, —O—CO—NH—, —S—, —SO—, —S(O)$_2$—, —S(O)$_2$O—, —CO—O—CH$_2$—CO—O— and the like. These may be contained as combination appropriately. These substituents also may be contained in a ring structure.

The alkyl group containing the divalent hetero atom-containing group includes: for example, an alkoxy group; an alkylcarbonyloxy group; an alkyl group having a heterocyclic structure such as a lactone structure, a sultone structure, a lactam structure and the like; and the like.

Furthermore, $R^1$ and $R^2$ may include an alkenyl group, an alkynyl group and the like in which at least one of carbon-carbon single bonds of these alkyl groups is substituted with a carbon-carbon double bond or a carbon-carbon triple bond.

The aryl group having 5 to 20 carbon atoms includes a monovalent aromatic hydrocarbon group such as a phenyl group, a naphthyl group, an anthracenyl group, a phenanthrenyl group, an azulenyl group and the like. The aryl group may be a monovalent aromatic heterocyclic group containing a hetero atom instead of a carbon atom in the ring of the aromatic hydrocarbon group. The aromatic heterocyclic group includes a monovalent aromatic heterocyclic group having a skeleton such as furan, thiophene, pyran, chromene, thianthrene, dibenzothiophene, xanthene and the like.

The substituent of $R^1$ and $R^2$ includes, a linear or alicyclic alkyl group (—$R^{Sp}$); a linear or alicyclic alkenyl group; a group containing, in the skeleton thereof, one heteroatom-containing group selected from the group consisting of —O—, —CO—, —COO—, —OCO—, —O—CO—O—, —NHCO—, —CONH—, —NH—CO—O—, —O—CO—NH—N(—$R^{Sp}$)—, —N(—$Ar^{Sp}$)—S—, —SO— and —$SO_2$—, instead of at least one methylene group in the alkyl group and the alkenyl group; an aryl group (—$Ar^{Sp}$); a hydroxy group; a halogen atom; and the like.

$R^{Sp}$ may include a linear, branched or cyclic alkyl group. $Ar^{Sp}$ may include: an aromatic hydrocarbon group having 12 or less carbon atoms such as a phenyl group, a naphthyl group and the like; and an aromatic heterocyclic group which may contain a hetero atom in the ring structure thereof instead of a carbon atom. When $R^1$ and $R^2$ have the substituent, a total number of carbon atoms in each of $R^1$ and $R^2$ is, including the substituent, preferably 1 to 20, more preferably 5 to 15, still more preferably 6 to 10.

Each of the alkyl group ($R^{Sp}$), the alkenyl group and the aryl group ($Ar^{Sp}$) as the substituent include the same groups as each of the alkyl group, the alkenyl group and the aryl group of the above $R^1$ to $R^2$.

The halogen atom as the substituent include a fluorine atom, a chlorine atom, a bromine atom and the like.

$R^1$ is preferably a methyl group, an n-butyl group, an aryl group and the like.

$R^2$ is preferably a methyl group, an ethyl group, an n-propyl group, an isopropyl group, an n-butyl group, a t-butyl group, an n-pentyl group, an n-hexyl group, a cyclopentyl group, a cyclohexyl group, an adamantyl group, an aryl group and the like.

$Ar^1$ is an arylene group having 5 to 20 carbon atoms, and $Ar^1$ includes those in which the aryl group as $R^1$ and $R^2$ becomes divalent. A substituent of the arylene group as $Ar^1$ includes the same substituent as those of $R^1$ and $R^2$. When $Ar^1$ has the substituent, a total number of carbon atoms in $Ar^1$ is, including the substituent, preferably 5 to 20, more preferably 5 to 16, and still more preferably 5 to 13.

$Ar^1$ is preferably a phenyl group, a naphthyl group and the like.

M is any one selected from the group consisting of Ge, Sn and Pb. M is preferably Sn from the viewpoint of absorbance of EUV.

When M is Sn, $R^1$ is preferably a methyl, an n-butyl, a phenyl and the like from the viewpoint of solubility. Also, although each of $R^1$ may be different from each other, it is preferable that three $R^1$ bonded to M are the same as each other from the viewpoint of synthesis.

Any two or more of $R^1$ may be bonded to each other to form a ring structure with M bonded thereto, and the ring structure may contain a hetero atom.

Y is any one selected from the group consisting of an iodine atom, a sulfur atom, a selenium atom and a tellurium atom. When Y is the iodine atom, n is 1, and when Y is any one selected from the group consisting of the sulfur atom, the selenium atom and the tellurium atom, n is 2.

Any two or more of $Ar^1$ and two $R^2$ may be bonded to each other to form a ring structure with Y bonded thereto, and the ring structure may contain a hetero atom. When Y is any one selected from the group consisting of the sulfur atom, the selenium atom and the tellurium atom, examples of such a cation are as follows, but not limited thereto in the present invention.

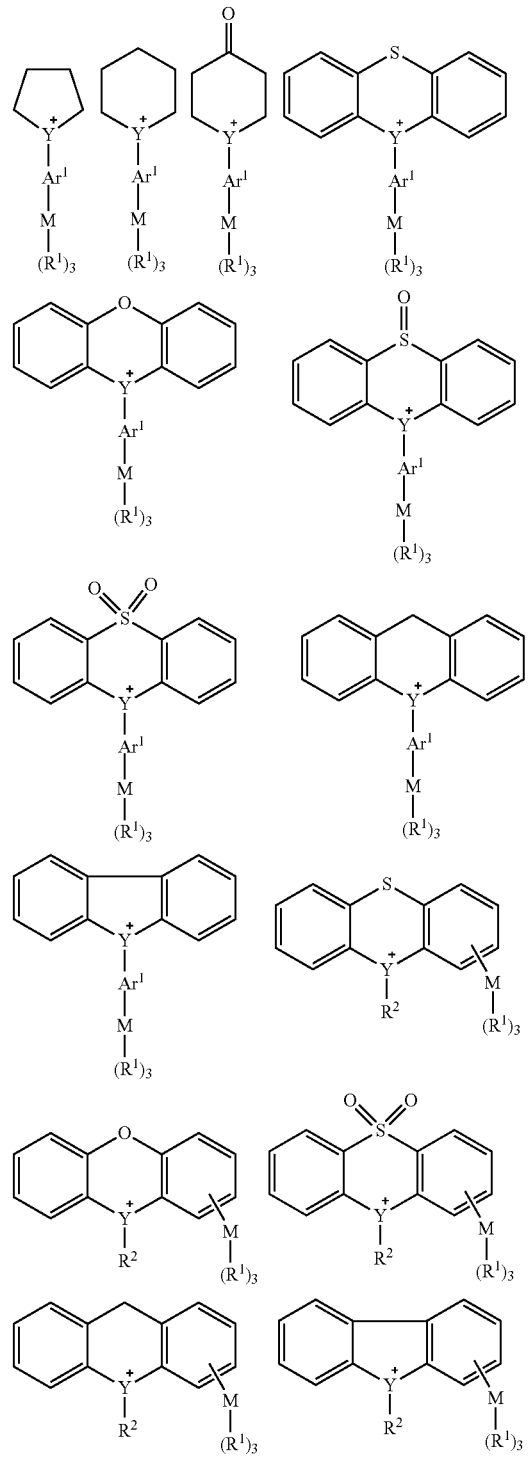

The metal-containing onium salt compound in one embodiment of the present invention is preferably an onium salt compound represented by the following Formula (2) or (3) in which Y is the iodine atom or the sulfur atom.

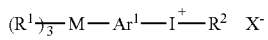

(2)

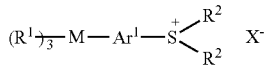

(3)

It is preferable that each of $R^1$, $R^2$, M, $Ar^1$ and $X^-$ in the above Formulae (2) and (3) are the same as each of $R^1$, $R^2$, M, $Ar^1$ and $X^-$ in the above Formula (1).

A specific structure of the iodonium cation of the onium salt compound represented by the above Formula (2) includes the following structures, but not limited thereto in the present invention.

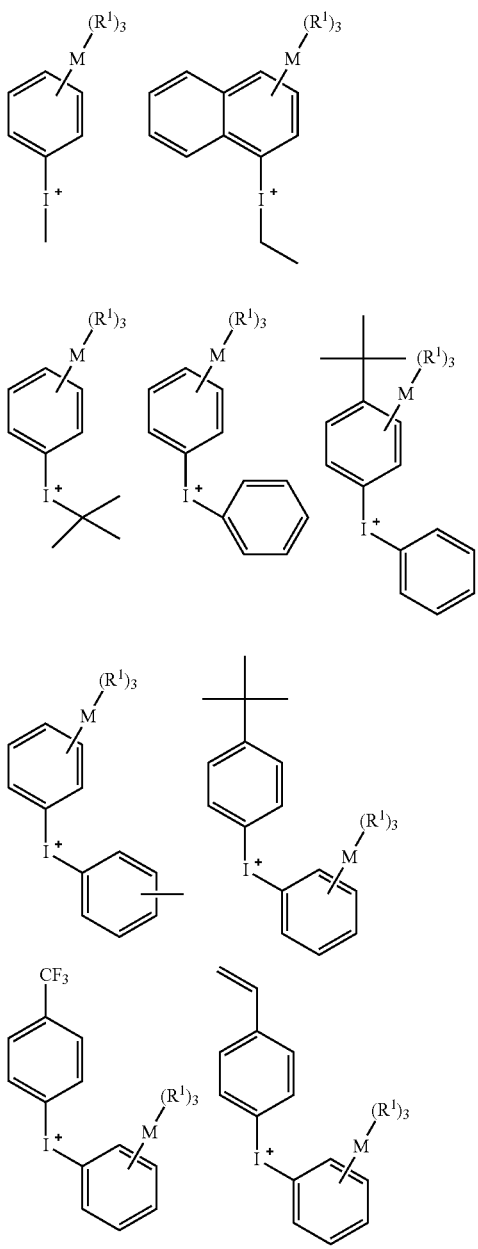

A specific structure of the sulfonium cation of the onium salt compound represented by the above Formula (3) includes the following structures, but not limited thereto in the present invention.

-continued
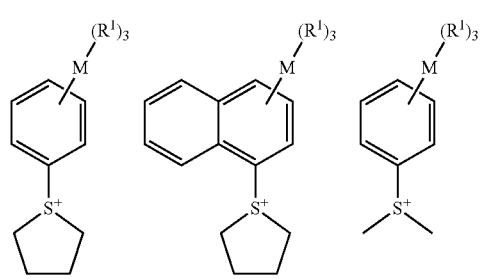
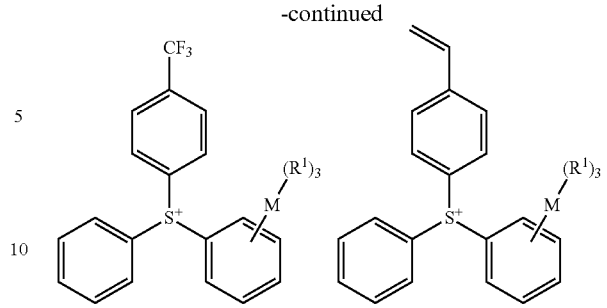
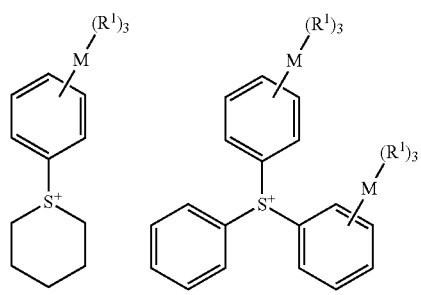
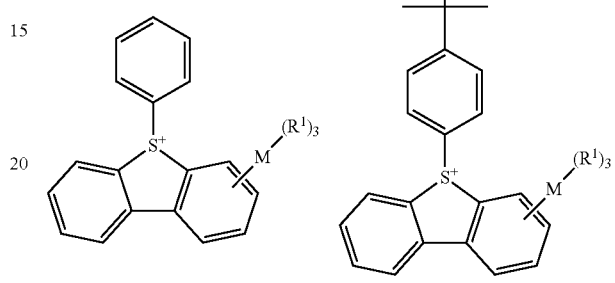
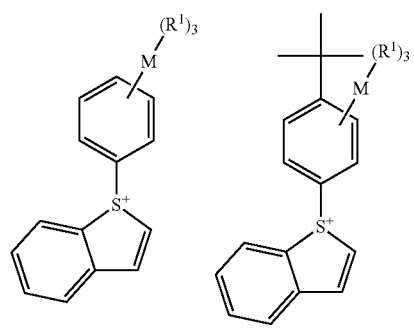
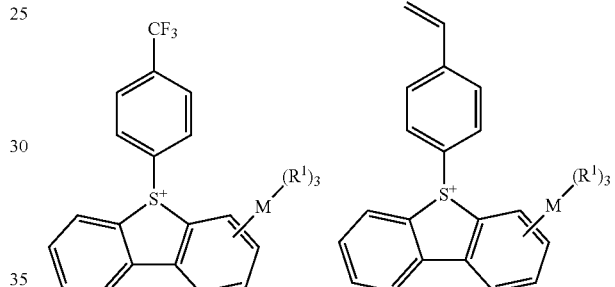
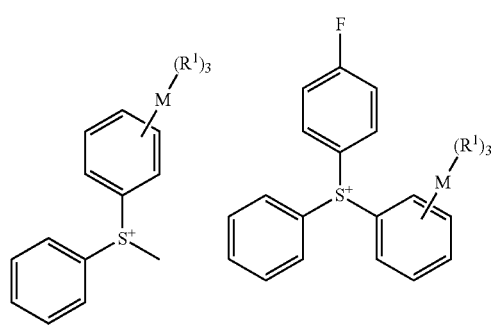
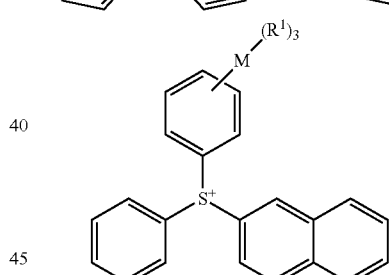
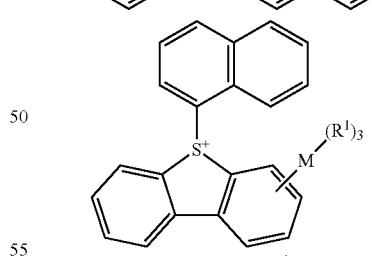
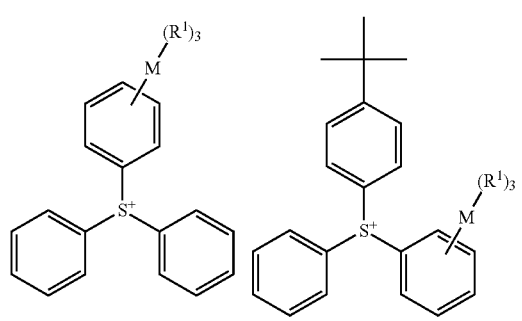
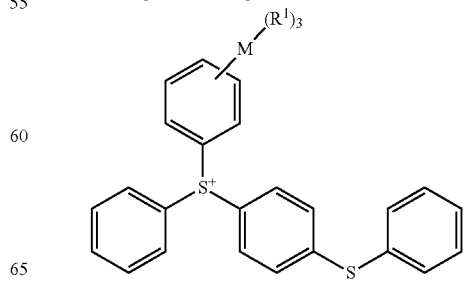

<1-2> Anion of Metal-Containing Onium Salt Compound $X^-$ is an anion. The anion may include a sulfonate anion, a carboxylate anion, an imide anion, a methide anion, a carbanion, a borate anion, a halogen anion, a phosphate anion, an antimonate anion an arsenate anion and the like, but not limited thereto.

More specifically, examples of the anion include preferably $ZA_a^-$, $(Rf)_b PF_{(6-b)}^-$, $R^4{}_c BA_{(4-c)}^-$, $R^4{}_c GaA_{(4-c)}^-$, $R^5 SO_3^-$, $(R^5 SO_2)_3 C^-$ and $(R^5 SO_2)_2 N^-$. Two Rf, two $R^4$ and two $R^5$ may be bonded to each other to form a ring.

Z represents a phosphorus atom, a boron atom or an antimony atom. A represents a halogen atom, preferably a fluorine atom.

P represents a phosphorus atom, F represents a fluorine atom, B represents a boron atom and Ga represents a gallium atom.

S represents a sulfur atom, O represents an oxygen atom, C represents a carbon atom and N represents a nitrogen atom.

Rf is preferably an alkyl group in which 80 mol % or more of hydrogen atoms thereof are substituted with fluorine atoms, and the alkyl group is preferably an alkyl group having 1 to 8 carbon atoms. The alkyl group to be Rf by the fluorination includes: a linear alkyl group such as methyl, ethyl, propyl, butyl, pentyl, octyl and the like; a branched alkyl group such as isopropyl, isobutyl, sec-butyl, tert-butyl and the like; a cycloalkyl group such as cyclopropyl, cyclobutyl, cyclopentyl, cyclohexyl and the like; and the like. In Rf, ratio of the hydrogen atoms substituted by fluorine atoms in the alkyl group is, based on the number of moles of hydrogen atoms in the original alkyl group, preferably 80 mol % or more, more preferably 90% or more, still more preferably 100%.

When the substitution ratio by the fluorine atoms is within these preferable ranges, photosensitivity of a sulfonium salt is further improved. Particularly preferable Rf includes $CF_3^-$, $CF_3CF_2^-$, $(CF_3)_2 CF^-$, $CF_3CF_2CF_2^-$, $CF_3CF_2CF_2CF_2^-$, $(CF_3)_2 CFCF_2^-$, $CF_3CF_2(CF_3)CF^-$ and $(CF_3)_3 C^-$. The b number of Rf are mutually independent, and therefore may be the same or different from each other.

$R^4$ represents a phenyl group in which a part of the hydrogen atoms is substituted with at least one halogen atom or electron withdrawing group. The halogen atom includes a fluorine atom, a chlorine atom, a bromine atom and the like. The electron withdrawing group includes a trifluoromethyl group, a nitro group, a cyano group and the like. Among these, a phenyl group in which one hydrogen atom thereof is substituted with the fluorine atom or the trifluoromethyl group is preferable. The c number of $R^4$ are mutually independent, and therefore may be the same or different from each other.

$R^5$ represents an alkyl group having 1 to 20 carbon atoms, a perfluoroalkyl group having 1 to 20 carbon atoms or an aryl group having 6 to 20 carbon atoms. The alkyl group and the perfluoroalkyl group may be a liner, a branched or cyclic, and the aryl group may be unsubstituted or may have a substituent.

a represents an integer of 4 to 6. b represents an integer of 1 to 5, preferably 2 to 4, more preferably 2 or 3. c represents an integer of 1 to 4, preferably 4.

The anion represented by $ZA_a^-$ includes anions represented by $SbF_6^-$, $PF_6^-$, $BF_4^-$ and the like.

The anion represented by $(Rf)_b PF_{(6-b)}^-$ includes anions represented by $(CF_3CF_2)_2 PF_4^-$, $(CF_3CF_2)_3 PF_3^-$, $((CF_3)_2 CF)_2 PF_4^-$, $((CF_3)_2 CF)_3 PF_3^-$, $(CF_3CF_2CF_2)_2 PF_4^-$, $(CF_3CF_2CF_2)_3 PF_3^-$, $((CF_3)_2 CFCF_2)_2 PF_4^-$, $((CF_3)_2 CFCF_2)_3 PF_3^-$, $(CF_3CF_2CF_2CF_2)_2 PF_4^-$, $(CF_3CF_2CF_2CF_2)_3 PF_3^-$ and the like. Among these, the anions represented by $(CF_3CF_2)_3 PF_3^-$, $(CF_3CF_2CF_2)_3 PF_3^-$, $((CF_3)_2 CF)_3 PF_3^-$, $((CF_3)_2 CF)_2 PF_4^-$, $((CF_3)_2 CFCF_2)_3 PF_3^-$ and $((CF_3)_2 CFCF_2)_2 PF_4^-$ are preferable.

The anion represented by $R^4{}_c BA_{(4-c)}^-$ includes anions represented by $(C_6 F_5)_4 B^-$, $((CF_3)_2 C_6 H_3)_4 B^-$, $(CF_3 C_6 H_4)_4 B^-$, $(C_6 F_5)_2 BF_2^-$, $C_6 F_5 BF_3^-$, $(C_6 H_3 F_2)_4 B^-$ and the like. Among these, the anions represented by $(C_6 F_5)_4 B^-$ and $((CF_3)_2 C_6 H_3)_4 B^-$ are preferable.

The anion represented by $R^4{}_c GaA_{(4-c)}^-$ includes anions represented by $(C_6 F_5)_4 Ga^-$, $((CF_3)_2 C_6 H_3)_4 Ga^-$, $(CF_3 C_6 H_4)_4 Ga^-$, $(C_6 F_5)_2 GaF_2^-$, $C_6 F_5 GaF_3^-$, $(C_6 H_3 F_2)_4 Ga^-$ and the like. Among these, the anions represented by $(C_6 F_5)_4 Ga^-$ and $((CF_3)_2 C_6 H_3)_4 Ga^-$ are preferable.

The anion represented by $R^5 SO_3^-$ includes those described in WO2011/093139. Specifically, a sulfonic acid derivative having an anion structure represented by the following Formula (a1) is preferable, but not limited thereto.

$$R^{5a}COOCH_2CH_2CFHCF_2SO_3^- \quad (a1)$$

In the above Formula (a), $R^{5a}$ represents a monovalent organic group having 1 to 20 carbon atoms which may have a substituent. The above organic group is preferably a group represented by the following Formula having 1 to 20 carbon atoms.

$$R^{5b}-(W-R^{5c}-)_m- \quad (a2)$$

In the above Formula (a2), $R^{5b}$ is any one of a monovalent group selected from the group consisting of an alkyl group and an aryl group. The alkyl group for $R^{5b}$ is the same as the alkyl group of $R^1$ and $R^2$. The aryl group includes the same as the aryl group of $R^1$ and $R^2$.

In addition, each W represents independently a direct bond; or any one group selected from the group consisting of —O—, —CO—, —COO—, —OCO—, —O—CO—O—, —NHCO—, —CONH—, —NH—CO—O—, —O—CO—NH—, —NH—, —S— and —CO—O—$CH_2$—CO—O—.

Each $R^{5c}$ is independently any one divalent group selected from the group consisting of an alkylene group and an arylene group. The alkylene group of $R^{5c}$ includes those in which the alkyl group of each of $R^1$ and $R^2$ becomes divalent. The arylene group of $R^{5c}$ includes those in which the aryl group of each of $R^1$ and $R^2$ becomes divalent.

In the above Formula (a2), m is 0 or an integer of 1 to 10. m is preferably 0 to 5, and more preferably 0 to 3.

When $R^{5a}$ has a substituent, a total number of carbon atoms in $R^{5a}$ is, including the substituent, preferably 1 to 200, more preferably 1 to 100, even more preferably 1 to 30, and still more preferably 3 to 30.

The substituent which $R^{5a}$ may have includes a hydroxy group, a carboxyl group, an alkoxy group, an acyl group, an alkoxycarbonyl group, an aryl group, an aryloxy group, a phosphino group, an alkylthio group, an arylthio group and the like, but not limited thereto.

The anion represented by $R^5 SO_3^-$ includes, other than the anion represented by the above Formula (a1), a trifluoromethanesulfonate anion, a pentafluoroethanesulfonate anion, a heptafluoropropanesulfonate anion, a nonafluorobutanesulfonate anion, a pentafluorophenylsulfonate anion, a p-toluenesulfonate anion, a benzenesulfonate anion, a camphorsulfonate anion, a methanesulfonate anion, an ethanesulfonate anion, a propanesulfonate anion, a butanesulfonate anion and the like. Among these, the trifluoromethanesulfonate anion, the nonafluorobutanesulfonate anion, the methanesulfonate anion, the butanesulfonate anion, the benzenesulfonate anion, the p-toluenesulfonate anion and the like are included.

The anion represented by $(R^5SO_2)_3C^-$ includes anions represented by $(CF_3SO_2)_3C^-$, $(C_2F_5SO_2)_3C^-$, $(C_3F_7SO_2)_3C^-$, $(C_4F_9SO_2)_3C^-$ and the like.

The anion represented by $(R^5SO_2)_2N^-$ includes anions represented by $(CF_3SO_2)_2N^-$, $(C_2F_5SO_2)_2N^-$, $(C_3F_7SO_2)_2N^-$, $(C_4F_9SO_2)_2N^-$ and the like. In addition, the anion represented by $(R^5SO_2)_2N^-$ also includes a cyclic imide in which moieties corresponding to two $(R^5SO_2)$ are bonded to each other to form a ring structure.

As a monovalent anion other than the above anions: a perhalogenate ion such as $ClO_4^-$, $BrO_4^-$ and the like; a halogenated sulfonate ion such as $FSO_3^-$, $ClSO_3^-$ and the like; a sulfate ion such as $CH_3SO_4^-$, $CF_3SO_4^-$, $HSO_4^-$ and the like; a carbonate ion such as $HCO_3^-$, $CH_3CO_3^-$ and the like; an aluminate ion such as $AlCl_4^-$, $AlF_4^-$ and the like; a hexafluorobismuthate ion $(BiF_6^-)$; a carboxylate ion such as $CH_3COO^-$, $CF_3COO^-$, $C_6H_5COO^-$, $CH_3C_6H_4COO^-$, $C_6F_5COO^-$, $CF_3C_6H_4COO^-$ and the like; an aryl borate ion such as $B(C_6H_5)_4^-$, $CH_3CH_2CH_2CH_2B(C_6H_5)_3^-$ and the like; a thiocyanate ion $(SCN^-)$; a nitrate ion $(NO_3^-)$; and the like may be used.

Among these anions, the sulfonate anion, carboxylate anion and the like are preferable.

When the resist composition contains the photoacid generator and the metal-containing onium salt compound, it is preferable to use an anion of the metal-containing onium salt compound having an acid strength thereof equal to or lower than that of the anion of the photoacid generator from the viewpoints of sensitivity and acid diffusion control because it acts as a photodegradable base. In addition, a balky anion structure is preferable as resolution is improved.

More specifically, pKa is preferably −2 to 6.

The pKa is a value obtained by analysis using ACD labs, manufactured by Fujitsu Limited.

<1-3> Metal-Containing Onium Salt Compound

The metal-containing onium salt compound may be added to the resist composition as a low molecular weight component, and it may be a polymer contained as a unit. That is, the compound represented by the above Formula (1) may be contained as a unit in the polymer so as to be bonded to the polymer main chain at any position of $R^1$, $R^2$ and $Ar^1$ of the compound. For example, in the case of the compound represented by the above Formula (1), it is preferable to have a bonding hand bonded to the polymer main chain directly or via a linking group instead of one H in $R^1$ of the cation moiety. When the metal-containing onium salt compound is a polymer, it may be bonded to the polymer main chain directly or via a linking group at the anion moiety instead of the cation moiety.

The unit constituting the polymer is preferably derived from a monomer having a radically polymerizable group such as a vinyl group, an isopropenyl group, an acryloxy group, a methacryloxy group and the like. The polymer may be a polymer including units other than the unit corresponding to the metal-containing onium salt compound. Details will be described later.

When the metal-containing onium salt compound is the polymer, the preferable number of carbons of $R^1$, $R^2$ and $Ar^1$ in the Formula (1) excludes a carbon number of the polymer main chain.

A specific structure of the onium salt compound represented by the above Formula (1) includes the following structures. The present invention is not limited to the onium salt compounds represented below including a substitution position corresponding to M.

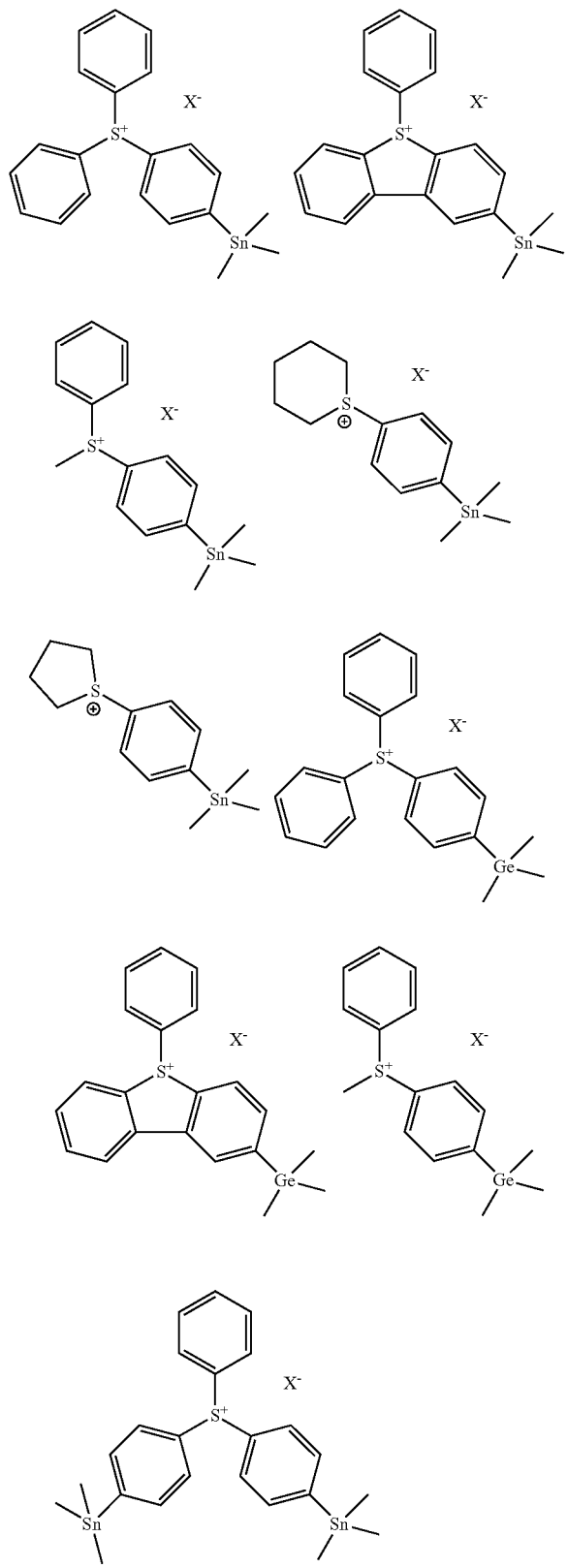

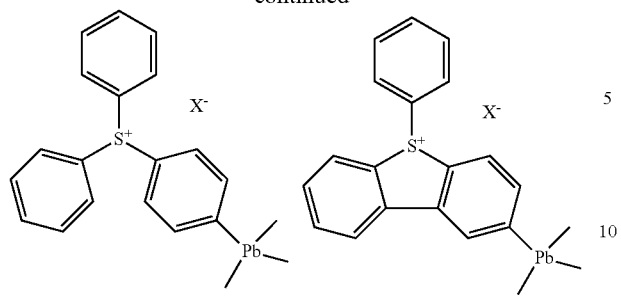

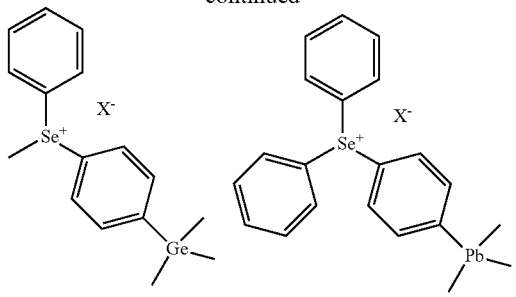

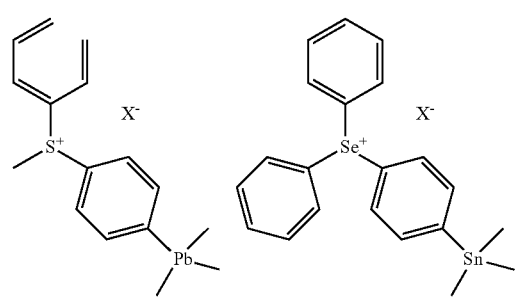

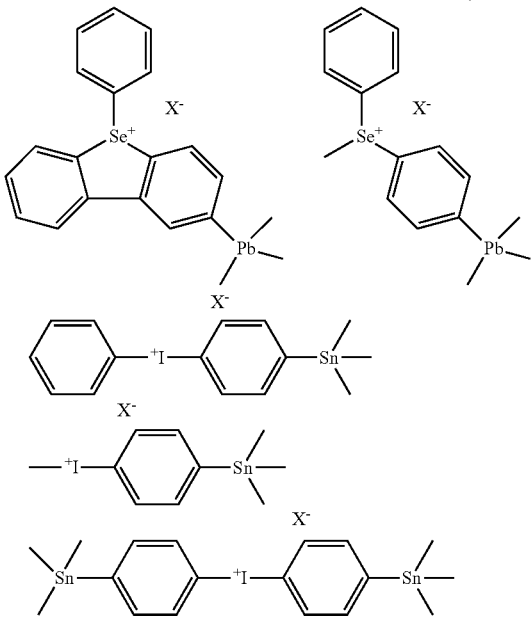

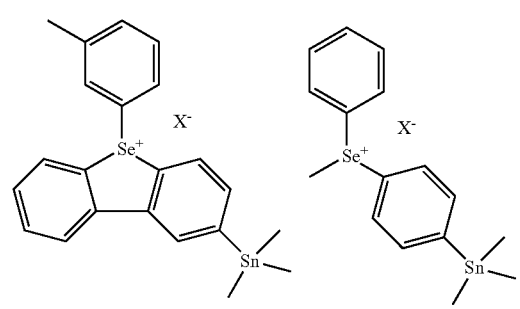

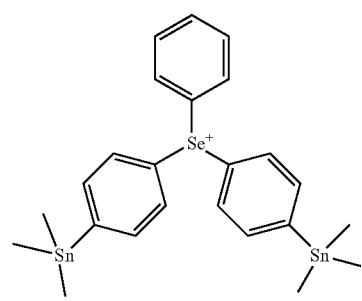

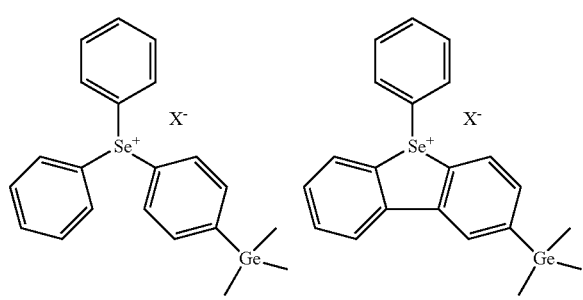

<1-4> Method for Manufacturing Metal-Containing Onium Salt Compound

The metal-containing onium salt compound according to one embodiment of the present invention can be synthesized by the following method.

In the following, a synthesis example of a tin-containing sulfonium salt in which $Ar^1$ in the above Formula (1) is a phenylene group, Y is a sulfur atom and M is Sn is described. A tetrahydrofuran (THF) solution of magnesium is heated to 40 to 50° C., and then a THF solution of a bromobenzene having $R^{2a}S$— group is added dropwise thereto. A THF solution of a trisubstituted organotin chloride having $R^1$ group is added dropwise thereto at 50° C. or lower, and a reaction is carried out for 1 to 3 hours by Grignard reaction to obtain a tin-containing sulfide.

The tin-containing sulfide is oxidized using meta-chloroperbenzoic acid (MCPBA) or the like to obtain a tin-containing sulfoxide. Thereafter, using a bromide having $R^{2b}$ group, magnesium and trimethylchlorosilane, a Cl salt of tin-containing sulfonium is obtained by the Grignard reaction. Subsequently, by salt exchange or the like, a tin-containing sulfonium salt compound having a corresponding $X^-$ can be obtained.

$R^1$ in the following synthesis example corresponds to $R^1$ in the above Formula (1), and each of $R^{2a}$ and $R^{2b}$ correspond to $R^2$ in the above Formula (1).

Those in which M is Ge or Pb can be synthesized in the same procedure as described above.

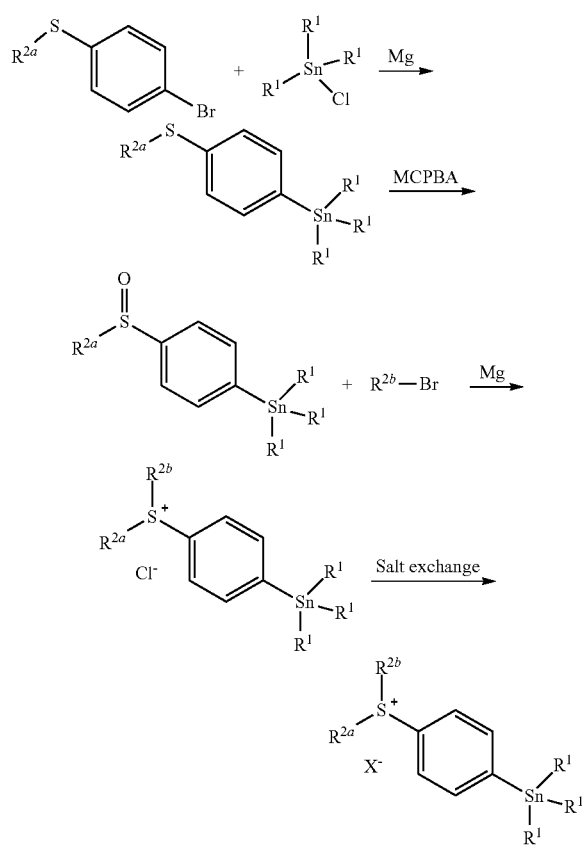

When Y is Se, it can be synthesized as follows. A THF solution of 1-bromo-4-chlorobenzene is cooled to −78° C., and then n-butyllithium is added dropwise thereto. A THF solution of diphenyl diselenide is added dropwise thereto to obtain 4-chlorophenyl phenyl selenide. Subsequently, a THF solution of magnesium is heated to 40 to 50° C., a THF solution of an organotin chloride having three $R^1$ groups is added dropwise thereto at 50° C. or lower, and then a reaction is carried out for 1 to 3 hours by the Grignard reaction to obtain a tin-containing selenide.

The tin-containing selenide, diphenyliodonium methylsulfate, anisole and copper (II) benzoate monohydrate are mixed and a reaction is carried out at 100° C. for 1 hour to obtain a tin-containing selenonium methylsulfate. Subsequently, by salt exchange or the like, a tin-containing selenonium salt compound having a corresponding $X^-$ can be obtained. When Y is Te, it can be synthesized in the same procedure as that of Se.

When Y is I, it can be synthesized as follows. Firstly, 1-bromo-4-iodobenzene, trifluoromethanesulfonic acid, benzene and dichloromethane are mixed and cooled to 0° C. A dichloromethane solution of MCPBA is added dropwise thereto and then a reaction is carried out for 1 hour to obtain 4-bromophenylphenyliodonium trifluoromethanesulfonate. Secondly, a THF solution of magnesium is heated to 40 to 50° C., and then a THF solution of 4-bromophenylphenyl iodonium trifluoromethanesulfonate is added dropwise thereto. A THF solution of an organotin chloride having three $R^1$ groups is added dropwise thereto at 50° C. or lower and a reaction is carried out for 1 to 3 hours by the Grignard reaction to obtain a tin-containing iodonium. Finally, by salt exchange or the like, a tin-containing iodonium salt compound having a corresponding $X^-$ can be obtained.

<2> Photodegradable Base

Some embodiments of the present invention are a photodegradable base containing the metal-containing onium salt compound.

As described above, the metal-containing onium salt compound in some embodiments of the present invention may be a polymer. When the metal-containing onium salt compound is the polymer, the polymer may be a homopolymer or a copolymer including another unit as long as it contains a unit functioning as a photodegradable base. When it is the copolymer, examples of the other unit include a unit acting as an acid-reactive compound, a hydroxyaryl group-containing unit and the like. The unit acting as the acid-reactive compound, the hydroxyaryl group-containing unit and the like will be described later.

<3> Resist Composition

One embodiment of the present invention relates to a resist composition including the above-described photodegradable base. It is preferable that the resist composition further contains a photoacid generator and an acid-reactive compound.

A content of the above photodegradable base in the resist composition of one embodiment of the present invention is preferably 0.5 to 30 parts by mass, more preferably 1 to 20 parts by mass, and still more preferably 2 to 10 parts by mass, with respect to 100 parts by mass of the acid-reactive compound described later.

When the resist composition contains the photoacid generator, the content of the photodegradable base in the resist composition is preferably 1 to 50 parts by mass, and more preferably 3 to 25 parts by mass, with respect to 10 parts by mass of the photoacid generator. By including the photodegradable base within the above-described range in the resist composition, it is possible to have characteristics superior in the sensitivity, resolution and pattern forming ability.

In calculation of the content, an organic solvent is not included as component of the resist composition.

When the above-described photodegradable base is bonded to the polymer, it is based on a mass excluding the polymer main chain.

The photodegradable base may be used solely or in combination of two or more.

Each component contained in the resist composition will be described below.

<3-1> Photoacid Generator

The resist composition according to some embodiments of the present invention preferably contains the photoacid generator.

The photoacid generator is not particularly limited as long as it is used in general resist compositions, and examples thereof include: an onium salt compound such as a sulfonium salt, an iodonium salt and the like; an N-sulfonyloxyimide compound; an oxime sulfonate compound; an organic halogen compound; a sulfonyldiazomethane compound; and the like. These can be used solely or in combination of two or more.

The sulfonium salt includes those described in WO2011/093139.

As described above, it is preferable to use an anion possessed in the photoacid generator having a higher acid strength than that of the anion of the metal-containing onium salt compound used as the photodegradable base.

More specifically, the photoacid generator has preferably pKa of −3 or lower. Such an anion includes a fluorine-substituted sulfonic acid and the like.

The photoacid generator may be added to the resist composition as a low molecular weight component, and may be contained as a polymer unit. That is, it may be contained as a unit in the polymer so as to be bonded to the polymer main chain at any position of the photoacid generator. For example, when the photoacid generator is the sulfonium salt, it is preferable to have a bonding hand bonded to the polymer main chain directly or via a linking group instead of one H which is one of a substituent in the sulfonium salt.

The content of the photoacid generator in the resist composition of one embodiment of the present invention is preferably 1 to 50 parts by mass, more preferably 3 to 30 parts by mass, and still more preferably 5 to 25 parts by mass, with respect to 100 parts by mass of the acid reactive compound described below.

When the photoacid generator is bonded to the polymer, it is based on a mass excluding the polymer main chain.

<3-2> Acid-Reactive Compound

The resist composition of some embodiments of the present invention preferably contains the acid-reactive compound in addition to the photodegradable base.

Preferably, the acid-reactive compound has a protecting group to be deprotected by acid, or is polymerized or crosslinked by acid. That is, the acid reactive compound is preferably at least one selected from the group consisting of a compound having a protecting group to be deprotected by acid, a compound having a polymerizable group to be polymerized by acid and a crosslinking agent exerting a crosslinking action by acid.

The compound having the protecting group to be deprotected by acid is a compound in which the protecting group is deprotected by an acid to generate a polar group and change solubility thereof in a developing solution. For example, in the case of aqueous development using an alkaline developer or the like, the compound having the protecting group to be deprotected by acid is insoluble in the alkaline developing solution, but becomes soluble in the alkaline developing solution when the protecting group of the compound in an exposed portion is deprotected by the acid generated from the photoacid generator by exposure.

In some embodiments of the present invention, the developing solution is not limited to the alkaline developing solution, and may be a neutral developing solution or an organic solvent developing solution. Therefore, in the case of using the organic solvent developing solution, the compound having the protecting group to be deprotected by acid is a compound whose solubility to be lowered in the organic solvent developing solution when the protecting group of the compound in an exposed portion is deprotected by the acid generated from the photoacid generator by the exposure to generate a polar group.

The polar group includes a hydroxy group, a carboxy group, an amino group, a sulfo group and the like.

Specific examples of the protective group to be deprotected by acid include: a group forming a tertiary alkyl ester group with a carboxy group; an alkoxy acetal group; a tetrahydropyranyl group; a siloxy group; a benzyloxy group; and the like. As the compound having the protecting group, a compound having a styrene, methacrylate, acrylate skeleton or the like in which these protecting groups are bonded is preferably used.

The compound having the protecting group to be deprotected by acid may be a low molecular compound containing the protecting group, and may be a polymer containing the protecting group. In some embodiments of the present invention, the low molecular compound has weight-average molecular weight of less than 2000, and the polymer has weight-average molecular weight of 2000 or more.

The compound having the polymerizable group to be polymerized by acid is a compound changing its solubility in a developing solution by polymerization by an acid. For example, in the case of the aqueous development, the compound having the polymerizable group to be polymerized by acid is soluble in an aqueous developing solution, whereas the compound after the polymerization has low solubility in the aqueous developing solution. Specific examples thereof include a compound having an epoxy group, a vinyloxy group, an oxetanyl group and the like.

The compound having the polymerizable group to be polymerized by acid may be a polymerizable low molecular compound or a polymerizable polymer.

The crosslinking agent exerting the crosslinking action by acid is a compound changing its solubility in a developing solution by crosslinking by an acid. For example, in the case of the aqueous development, the crosslinking agent exerting the crosslinking action by acid is soluble in an aqueous developing solution, whereas the compound after the polymerization or the crosslinking has low solubility in the aqueous developing solution. Specific examples thereof include a crosslinking agent having an epoxy group, a vinyloxy group, a 1-alkoxyamino group, an oxetanyl group and the like. When the compound is the crosslinking agent exerting the crosslinking action, a compound to be crosslinked, that is, a compound reacting with the crosslinking agent to change solubility thereof in the developing solution includes a compound having a phenolic hydroxyl group and the like.

The compound exerting the crosslinking action by acid may be a polymerizable low molecular compound or a polymerizable polymer.

When the acid-reactive compound is the polymer, in addition to the unit binding the acid-reactive compound, another unit commonly used in the resist composition may be contained in the polymer. For example, the other unit include: a unit (I) having at least one skeleton selected from the group consisting of a lactone skeleton, a sultone skeleton and a lactam skeleton and the like; a unit (II) having a group having at least one bond selected from the group consisting of an ether bond, an ester bond and an acetal bond and the like, and a unit having a hydroxy group and the like; a hydroxyaryl group-containing unit (III); and the like. Furthermore, it may contain a unit (IV) binding the photodegradable base and a unit (V) binding the photoacid generator.

In some embodiments of the present invention, a ratio of each unit of the polymer is not particularly limited. When the unit binding the acid-reactive compound is included as a unit of the same polymer with other units, the unit binding the acid-reactive compound is preferably 10 to 70 mol %, more preferably 15 to 65 mol %, and still more preferably 20 to 60 mol % in the whole polymer unit.

A content of the unit (I) is preferably 0 to 60 mol %, more preferably 10 to 60 mol %, and still more preferably 20 to 60 mol % in the whole polymer unit. The unit (II) is preferably 0 to 70 mol %, more preferably 5 to 70 mol %, and still more preferably 10 to 60 mol % in the whole polymer unit. The content of the unit (III) is preferably 0 to 90 mol %, and more preferably 10 to 80 mol % in the whole polymer unit. The unit (IV) is preferably 0 to 30 mol %, more preferably 1 to 30 mol %, and still more preferably 3 to 20 mol % in the whole polymer unit. The unit (V) is preferably 0 to 30 mol %, more preferably 1 to 30 mol %, and still more preferably 3 to 20 mol % in the whole polymer unit.

<3-3> Other Components

In addition to the above-described components, the resist composition of one embodiment of the present invention may contain, as an optional component, an organic solvent, an acid diffusion control agent, a surfactant, an organic carboxylic acid, a dissolution inhibitor, a stabilizer, a dye, a sensitizer and the like used in ordinary resist compositions and a combination thereof, if necessary.

The organic solvent is preferably ethylene glycol monoethyl ether acetate, cyclohexanone, 2-heptanone, propylene glycol monomethyl ether (PGME), propylene glycol monomethyl ether acetate (PGMEA), propylene glycol monomethyl ether propionate, propylene glycol monoethyl ether acetate, methyl 3-methoxypropionate, ethyl 3-ethoxypropionate, methyl 3-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methyl pyrrolidone, N,N-dimethylformamide, γ-butyrolactone, N,N-dimethylacetamide, propylene carbonate, ethylene carbonate and the like, for example. These organic solvents are used solely or in combination.

The acid diffusion control agent has an effect of controlling undesirable chemical reactions in exposed portion by controlling diffusion phenomenon of the acid generated from the photoacid generator in the resist film. Thereby, storage stability of the obtained resist composition is further improved, the resolution of the resist is further improved, and change in linewidth of resist pattern due to variation in time elapsed from the exposure to the development process can be suppressed. Thereby, a resist composition excellent in process stability can be obtained.

The acid diffusion control agent includes a compound having one, two or three nitrogen atoms in the same molecule, an amide group-containing compound, a urea compound, a nitrogen-containing heterocyclic compound and the like. Further, as the acid diffusion control agent, it is also possible to use the photodegradable base other than the metal-containing onium salt compound of one embodiment of the present invention which generates a weak acid by the exposure. Specifically, compounds described in JP3577743B, JP2001-215689A, JP2001-166476A, JP2008-102383A, JP2010-243773A, JP 2011-37835A and JP2012-173505A are included.

When the acid diffusion control agent is contained, a content thereof is preferably 0.01 to 20 parts by mass, more preferably 0.03 to 15 parts by mass, and still more preferably 0.05 to 10 parts by mass, with respect to 100 parts by mass of the acid-reactive compound. The above content does not include the metal-containing onium salt compound of one embodiment of the present invention.

The surfactant is preferably used for improving coating property. The surfactant includes: a nonionic surfactant such as polyoxyethylene alkyl ethers, polyoxyethylene alkyl allyl ethers, a polyoxyethylene polyoxypropylene block copolymers, sorbitan fatty acid esters, polyoxyethylene sorbitan fatty acid esters; and the like; a fluorine-containing surfactant; an organosiloxane polymer; and the like.

A content of the surfactant is preferably from 0.0001 to 2 parts by mass, and more preferably from 0.0005 to 1 part by mass, with respect to 100 parts by mass of the acid-reactive compound.

The organic carboxylic acid includes an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, phthalic acid, terephthalic acid, isophthalic acid, 2-naphthoic acid, 1-hydroxy-2-naphthoic acid, 2-hydroxy-3-naphthoic acid and the like. When electron beam exposure is performed under vacuum, inside of writing chamber may be contaminated by volatilization from surface of a resist film. Therefore, an aromatic organic carboxylic acid, especially, benzoic acid, 1-hydroxy-2-naphthoic acid and 2-hydroxy-3-naphthoic acid are preferable.

A content of the organic carboxylic acid is preferably from 0.01 to 10 parts by mass, more preferably from 0.01 to 5 parts by mass, and still more preferably from 0.01 to 3 parts by mass, with respect to 100 parts by mass of the acid-reactive compound.

Components of the resist composition are dissolved in the above-described organic solvent and dissolved in preferably 1 to 40% by mass, more preferably 1 to 30% by mass, and still more preferably 3 to 20% by mass in the resist composition containing the organic solvent as solid content concentration.

When the resist composition of one embodiment of the present invention contains the polymer, weight-average molecular weight of the polymer is preferably 2,000 to 200,000, more preferably 2,000 to 50,000, and still more preferably 2,000 to 15,000. From the viewpoint of the sensitivity, preferable dispersity, molecular weight distribution (Mw/Mn), of the polymer is 1.0 to 2.2, and more preferably 1.2 to 2.0.

In some embodiments of the present invention, the weight-average molecular weight and dispersity of the polymer are defined as polystyrene equivalent value by GPC measurement.

The resist composition of one embodiment of the present invention may contain a fluorine-containing water repellent polymer.

The fluorine-containing water repellent polymer includes, but not limited to, a polymer generally used in an immersion exposure process, and is preferably a polymer having higher fluorine-atom content than that of the above polymer. Thereby, when the resist film is formed using the resist composition, the fluorine-containing water repellent polymer can be localized on the surface of the resist film due to water repellency of the fluorine-containing water repellent polymer.

As a fluorine content of the fluorine-containing water repellent polymer, it is preferably 25% or more of the hydrogen atoms in hydrocarbon groups in the fluorine-containing water repellent polymer is fluorinated, and more preferably 50% or more.

From the viewpoint of improving hydrophobicity of the resist film, a content of the fluorine-containing water repellent polymer in the resist composition is preferably 0.5 to 10 parts by mass with respect to 100 parts by mass of the polymer, which is not fluorine-repellent polymer, of one embodiment of the present invention. The fluorine-containing water repellent polymer may be used solely, or in combination of two or more.

The composition of one embodiment of the present invention is obtained by mixing each of the above components, and the mixing method is not particularly limited.

<4> Method for Manufacturing Device

One embodiment of the present invention is a method for manufacturing a device, including a resist film forming step, a photolithography step, and a pattern forming step, where in the resist film forming step, a resist film is formed by, for example, coating resist composition on a substrate, where in the photolithography step, the resist film is exposed, and where in the pattern forming step, the exposed resist film is developed to obtain a photoresist pattern.

One embodiment of the present invention may be a method for manufacturing a substrate having a pattern before obtaining individualized chips using the above resist composition, and the method includes the resist film forming step, the photolithography step, and the pattern forming step.

An active energy ray used for the exposure in the photolithography step may be any light capable of generating the acid by activation of the metal-containing onium salt compound of one embodiment of the present invention, which includes KrF excimer laser light, ArF excimer laser light, $F_2$ excimer laser light, electron beam, UV, visible light, X ray, electron beam, ion beam, i-line, EUV and the like.

In one embodiment of the present invention, the active energy ray used for the exposure in the photolithography step is preferably ionizing radiation such as electron beam (EB), the extreme ultraviolet (EUV) or the like.

Dose of the light varies depending on the kind and blending ratio of each component in photocurable composition, film thickness of the coating film and the like, but is preferably 1 J/cm$^2$ or less or 1000 μC/cm$^2$ or less.

When the resist composition contains the sensitizer compound or contains the corresponding sensitizer compound as a sensitizer unit in the polymer, it is also preferable to perform second exposure with ultraviolet or the like after the irradiation with the ionizing radiation such as EUV or the like.

EXAMPLES

Hereinafter, some embodiments of the present invention will be described based on examples. However, the present invention is not limited by these examples at all.

<Synthesis of Tin-Containing Sulfonium Salt>

[Synthesis Example 1] Synthesis of Tin-Containing Sulfide

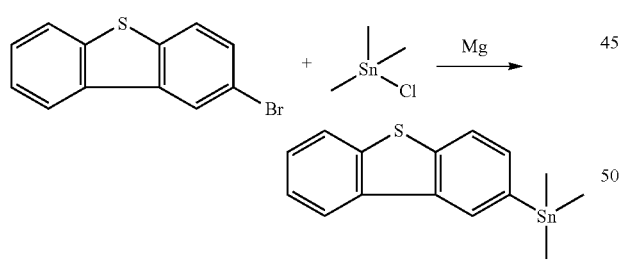

A solution of magnesium (1.71 g) in tetrahydrofuran (16.7 mL) is heated to 50° C. and then a solution of 2-bromodibenzothiophene (15.5 g) in tetrahydrofuran (33.0 mL) is added dropwise thereto. A solution of trimethyltin chloride (12.3 g) in tetrahydrofuran (6.0 mL) is added dropwise thereto at 30° C. or lower. After stirring for 1 hour, a saturated aqueous solution of ammonium chloride is added dropwise thereto to stop the reaction. After general aqueous work-up and solvent evaporation, purification is carried out by silica gel column chromatography (n-hexane/ethyl acetate=4/1) to obtain tin-containing sulfide (TMSnDBT) (17.0 g, yield 79%) as an oil.

[Synthesis Example 2] Synthesis of Tin-Containing Sulfoxide

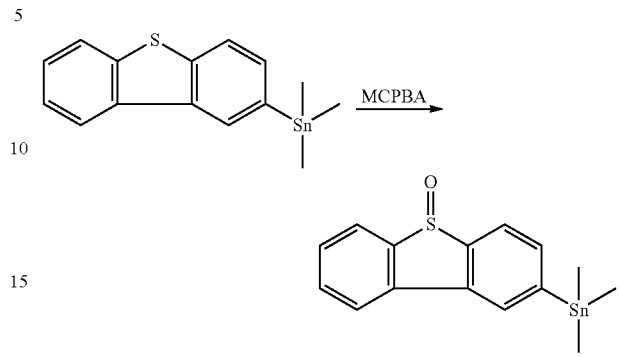

A solution of tin-containing sulfide (4.6 g) obtained in Synthesis Example 1 in dichloromethane (16.4 mL) is cooled to 10° C. or lower, and then a solution of MCPBA (3.32 g) in dichloromethane (17.1 mL) is added dropwise thereto. After stirring for 30 minutes, a 6 mass % sodium bicarbonate solution is added dropwise thereto to stop the reaction. After the general aqueous work-up and solvent evaporation, purification is carried out by silica gel column chromatography (n-hexane/ethyl acetate=10/1) to obtain tin-containing sulfoxide (PhTMSnDBTO) (3.0 g, yield 63%) as a white crystal.

[Synthesis Example 3] Synthesis of Chloride Salt of Tin-Containing Sulfonium

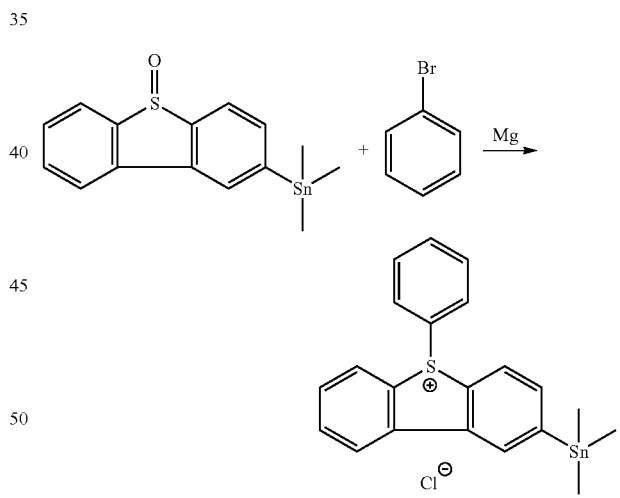

A solution of magnesium (0.4 g) in tetrahydrofuran (10.0 mL) is heated to 50° C., and then a solution of bromobenzene (2.14 g) in tetrahydrofuran (2.1 mL) is added dropwise thereto to prepare a Grignard reagent of phenylmagnesium bromide.

The Grignard reagent (6.9 mL) is added dropwise to a mixed solution of the tin-containing sulfoxide (2.0 g) obtained in Synthesis Example 2, trimethylchlorosilane (1.79 g) and tetrahydrofuran (24.0 g) at 30° C. or lower. After stirring for 1 hour, a saturated aqueous solution of ammonium chloride is added dropwise thereto to stop the reaction. After washing with water, a solvent is evaporated and then a residue is dissolved with water. After washing with ethyl acetate, then extracted with dichloromethane, and a solvent is evaporated to obtain a tin-containing sulfonium chloride salt (PhTMSnDBT-Cl) (0.6 g, yield 23%) as a white crystal.

[Synthesis Example 4] Synthesis of Tin-Containing Sulfonium Salt (PDB 1)

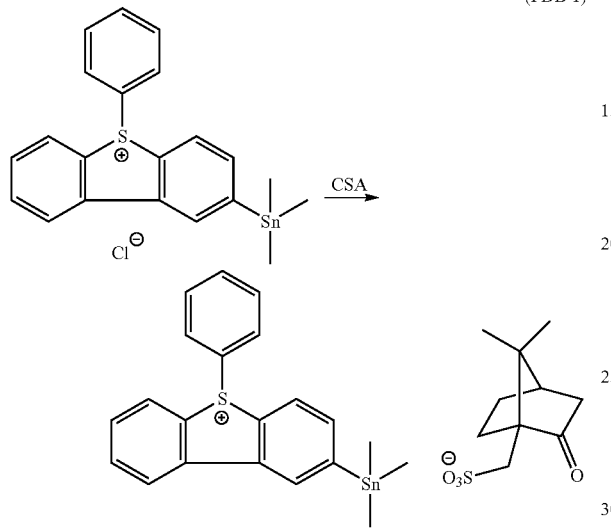

The tin-containing sulfonium chloride salt (0.4 g) obtained in Synthesis Example 3, camphorsulfonic acid (0.2 g), dichloromethane (4.0 mL) and water (2.3 mL) are mixed and stirred for 1 hour. After washing with water, it is crystallized with methyl-t-butyl ether to obtain PDB 1 (PhTMSnDBT-CSA) (0.57 g, yield 78%) as a white crystal.

[Synthesis Example 5] Synthesis of Tin-Containing Sulfonium Salt (PDB 2)

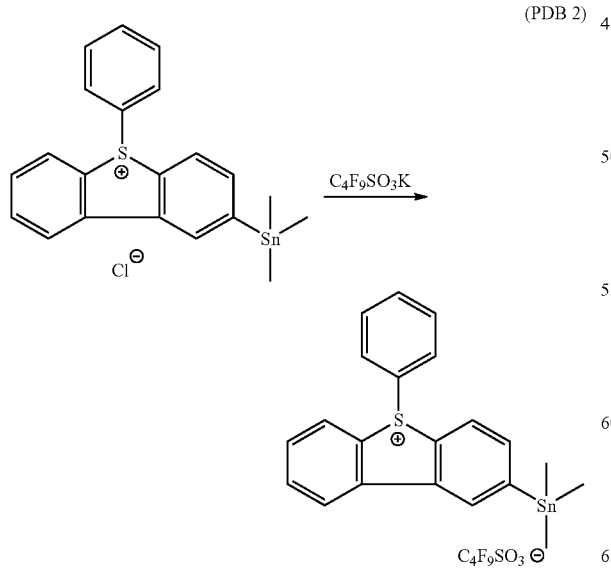

PDB 2 (PhTMSnDBT-PFBS) (0.3 g, yield 48%) as a white crystal is obtained in the same procedure as Synthesis Example 4, except that potassium nonafluorobutane-sulfonate (0.29 g) is used instead of camphorsulfonic acid (0.2 g).

[Synthesis Example 6] Synthesis of Tin-Containing Sulfonium Salt (PDB 3)

PDB 3 (PhTMSnDBT-AdTF) (0.69 g, yield 77%) as a white crystal is obtained in the same procedure as Synthesis Example 4, except that sodium 4-(1-adamantanecarbony-loxy) 1,1,2-trifluorobutane-1-sulfonate (0.34 g) is used instead of camphorsulfonic acid (0.2 g).

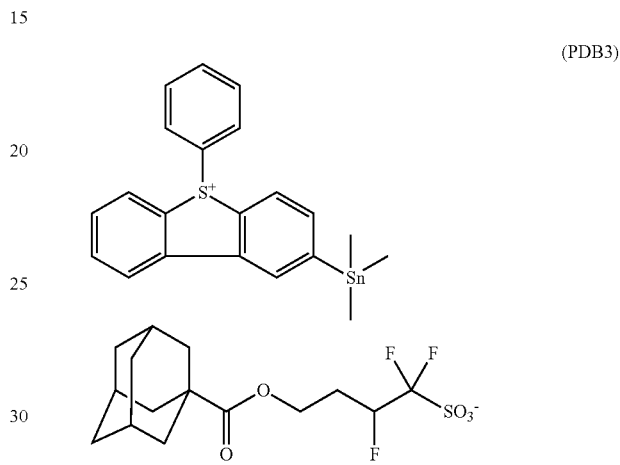

[Synthesis Example 7] Synthesis of Tin-Containing Sulfonium Salt (PDB 4)

PDB 4 (PhTMSnDBT-HAdTF) (0.55 g, yield 79%) as a white crystal is obtained in the same procedure as Synthesis Example 4, except that sodium 4-(3-hydroxy-1-adamantan-ecarbonyloxy) 1,1,2-trifluorobutane-1-sulfonate (0.35 g) is used instead of camphorsulfonic acid (0.2 g).

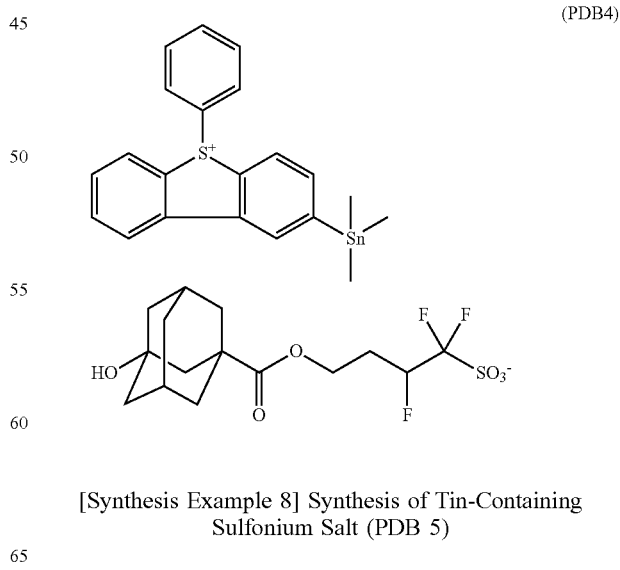

[Synthesis Example 8] Synthesis of Tin-Containing Sulfonium Salt (PDB 5)

PDB 5 (PhTBSnDBT-CAS) (0.54 g, yield 80%) as a white crystal is obtained in the same procedure as Synthesis Examples 1 to 4, except that tributyltin chloride (20.1 g) is used instead of trimethyltin chloride (12.3 g).

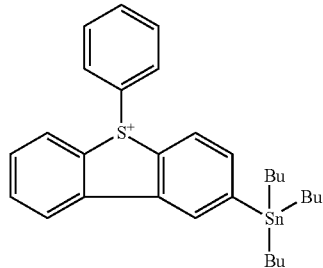
(PDB5)

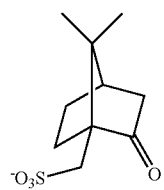

[Synthesis Example 9] Synthesis of Tin-Containing Sulfonium Salt (PDB 6)

PDB 6 (PhTBSnDBT-PFBS) (0.54 g, yield 80%) as a white crystal is obtained in the same procedure as Synthesis Example 8, except that potassium nonafluorobutane-sulfonate (0.29 g) is used instead of camphorsulfonic acid (0.2 g).

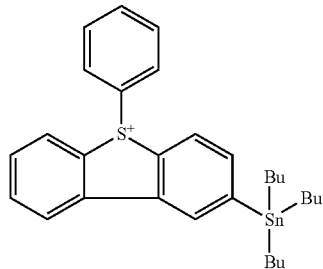
(PDB6)

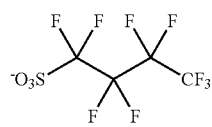

[Synthesis Example 10] Synthesis of Tin-Containing Sulfonium Salt (PDB 7)

PDB 7 (PhTBSnDBT-AdTF) (0.64 g, yield 80%) as a white crystal is obtained in the same procedure as Synthesis Example 8, except that sodium 4-(1-adamantanecarbonyloxy) 1,1,2-trifluorobutane-1-sulfonate (0.34 g) is used instead of camphorsulfonic acid (0.2 g).

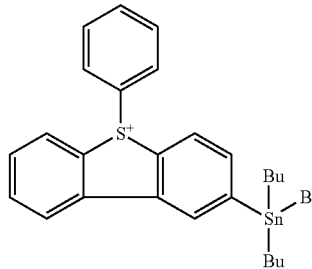
(PDB7)

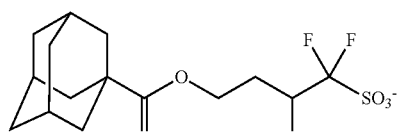

[Synthesis Example 11] Synthesis of Tin-Containing Sulfonium Salt (PDB 8)

PDB 8 (PhTMSnDBT-HAdTF) (0.64 g, yield 79%) as a white crystal is obtained in the same procedure as in Synthesis Example 8, except that sodium 4-(3-hydroxy-1-adamantanecarbonyloxy) 1,1,2-trifluorobutane-1-sulfonate (0.35 g) is used instead of camphorsulfonic acid (0.2 g).

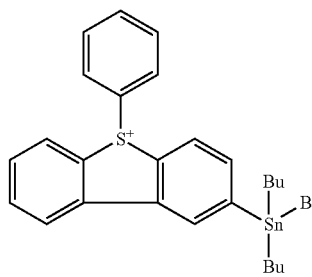
(PDB8)

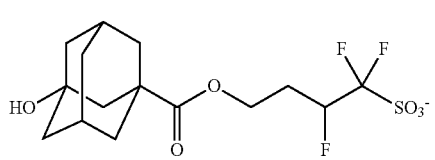

[Synthesis Example 12] Synthesis of Tin-Containing Sulfonium Salt (PDB 9)

PDB 9 (TMSnTPS-AdTF) (0.55 g, yield 80%) as a white crystal is obtained in the same procedure as Synthesis Examples 1 to 4, except that 4-bromodiphenyl sulfide (15.6 g) is used instead of 2-bromodibenzothiophene (15.5 g), and sodium 4-(1-adamantanecarbonyloxy) 1,1,2-trifluorobutane-1-sulfonate (0.33 g) is used instead of camphorsulfonic acid (0.2 g).

(PDB9)

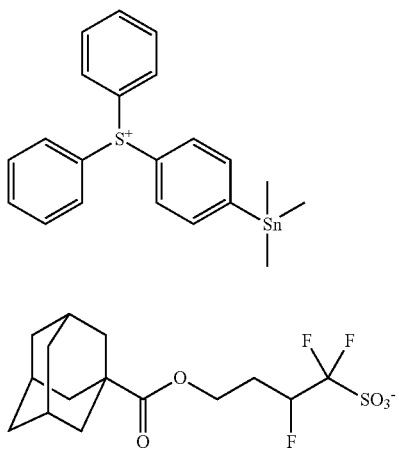

Example 1

<Preparation of Resist Composition>

100 parts by mass of Polymer (A-1), weight-average molecular weight: about 10,000, a=0.4, b=0.4, c=0.2 in the following Formulae, as a base polymer, 8 parts by mass of triphenylsulfonium nonafluorobutanesulfonate (B-1) as a photoacid generator, 5 parts by mass of Photodegradable Base (PDB 1) as an acid diffusion control agent, and 1,800 parts by mass of propylene glycol monomethyl ether acetate as a solvent are mixed and then filtered with a PTFE filter to prepare Radiation Sensitive Resist Composition (H-1) solution. Details of the resist composition are described in Table 1.

A monomer ratio of units of copolymer in some embodiments of the present invention is not limited to the following.

(A-1)

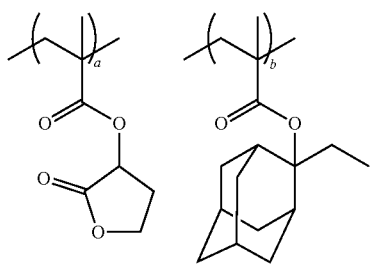

(A-2)

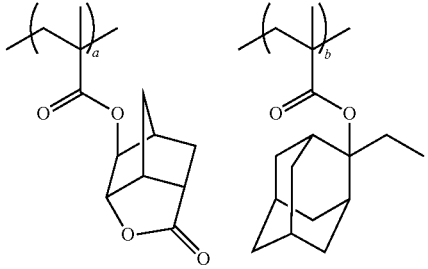

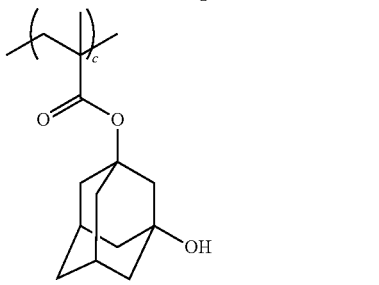

(A-3)

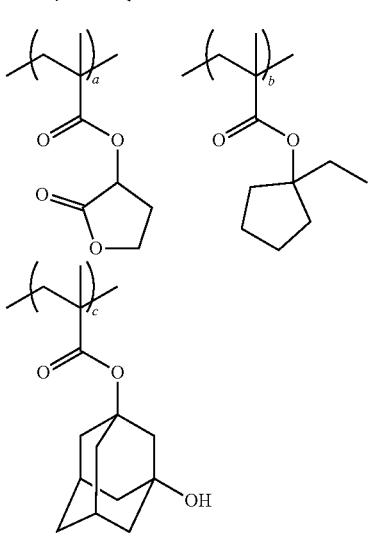

Examples 2 to 40

Radiation Sensitive Resist Compositions (H-2) to (H-40) are obtained in the same procedure as Example 1, except that any one of (A-1) to (A-3) instead of Polymer (A-1) as the base polymer, any one of (B-1) to (B-4) represented below instead of triphenylsulfonium nonafluorobutanesulfonate (B-1) as the photoacid generator, and any one of PDB 2 to PDB 9 instead of PDB 1 as the acid diffusion control agent are used in blending amount described in Table 1.

(B-1)

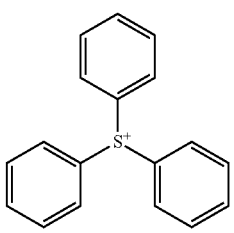

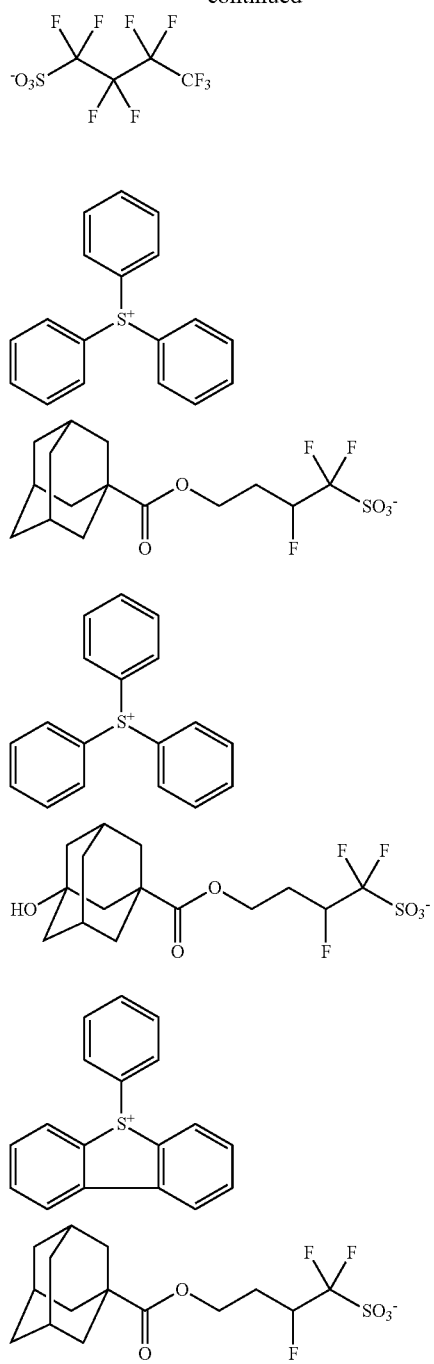

Comparative Examples 1 to 22

Radiation Sensitive Resist Compositions (H-37) to (H-52) are obtained in the same procedure as Example 1, except that any one of (A-1) to (A-3) instead of Polymer (A-1) as the base polymer, any one of (B-1) to (B-4) instead of triphenylsulfonium nonafluorobutanesulfonate (B-1) as the photoacid generator, and any one of PDB 10 to PDB 13 represented below instead of Photodegradable Base (PDB 1) as the acid diffusion control agent are used in the blending amount described in Table 1.

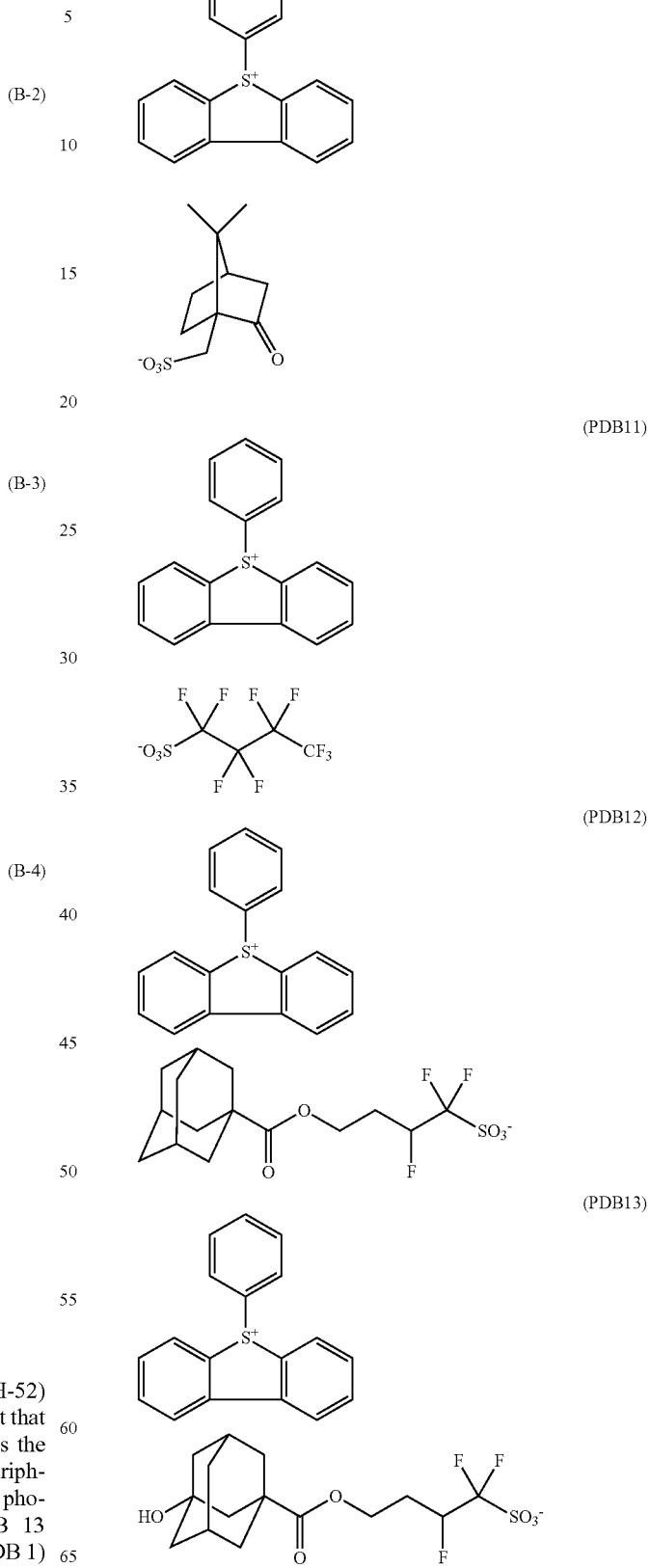

TABLE 1

| | Resist Composition | Polymer Type | Polymer Blend amount (part by mass) | Photoacid Generator Type | Photoacid Generator Blend amount (part by mass) | Photodegradable Base Type | Photodegradable Base Blend amount (part by mass) | Solvent Type | Solvent Blend amount (part by mass) |
|---|---|---|---|---|---|---|---|---|---|
| Example 1 | H-1 | A-1 | 100 | B-1 | 8.0 | PDB1 | 5.0 | D-1 | 1800 |
| Example 2 | H-2 | A-1 | 100 | B-1 | 8.0 | PDB2 | 5.5 | D-1 | 1800 |
| Example 3 | H-3 | A-1 | 100 | B-1 | 8.0 | PDB3 | 6.1 | D-1 | 1800 |
| Example 4 | H-4 | A-1 | 100 | B-1 | 8.0 | PDB4 | 6.2 | D-1 | 1800 |
| Example 5 | H-5 | A-1 | 100 | B-1 | 8.0 | PDB5 | 6.0 | D-1 | 1800 |
| Example 6 | H-6 | A-1 | 100 | B-1 | 8.0 | PDB6 | 6.5 | D-1 | 1800 |
| Example 7 | H-7 | A-1 | 100 | B-1 | 8.0 | PDB7 | 7.0 | D-1 | 1800 |
| Example 8 | H-8 | A-1 | 100 | B-1 | 8.0 | PDB8 | 7.1 | D-1 | 1800 |
| Example 9 | H-9 | A-1 | 100 | B-1 | 8.0 | PDB9 | 6.1 | D-1 | 1800 |
| Example 10 | H-10 | A-1 | 100 | B-2 | 9.0 | PDB1 | 5.0 | D-1 | 1800 |
| Example 11 | H-11 | A-1 | 100 | B-2 | 9.0 | PDB2 | 5.5 | D-1 | 1800 |
| Example 12 | H-12 | A-1 | 100 | B-2 | 9.0 | PDB3 | 6.1 | D-1 | 1800 |
| Example 13 | H-13 | A-1 | 100 | B-2 | 9.0 | PDB4 | 6.2 | D-1 | 1800 |
| Example 14 | H-14 | A-1 | 100 | B-2 | 9.0 | PDB5 | 6.0 | D-1 | 1800 |
| Example 15 | H-15 | A-1 | 100 | B-2 | 9.0 | PDB6 | 6.5 | D-1 | 1800 |
| Example 16 | H-16 | A-1 | 100 | B-2 | 9.0 | PDB7 | 7.0 | D-1 | 1800 |
| Example 17 | H-17 | A-1 | 100 | B-2 | 9.0 | PDB8 | 7.1 | D-1 | 1800 |
| Example 18 | H-18 | A-1 | 100 | B-2 | 9.0 | PDB9 | 6.1 | D-1 | 1800 |
| Example 19 | H-19 | A-1 | 100 | B-3 | 9.2 | PDB1 | 5.0 | D-1 | 1800 |
| Example 20 | H-20 | A-1 | 100 | B-3 | 9.2 | PDB2 | 5.5 | D-1 | 1800 |
| Example 21 | H-21 | A-1 | 100 | B-3 | 9.2 | PDB3 | 6.1 | D-1 | 1800 |
| Example 22 | H-22 | A-1 | 100 | B-3 | 9.2 | PDB4 | 6.2 | D-1 | 1800 |
| Example 23 | H-23 | A-1 | 100 | B-3 | 9.2 | PDB5 | 6.0 | D-1 | 1800 |
| Example 24 | H-24 | A-1 | 100 | B-3 | 9.2 | PDB6 | 6.5 | D-1 | 1800 |
| Example 25 | H-25 | A-1 | 100 | B-3 | 9.2 | PDB7 | 7.0 | D-1 | 1800 |
| Example 26 | H-26 | A-1 | 100 | B-3 | 9.2 | PDB8 | 7.1 | D-1 | 1800 |
| Example 27 | H-27 | A-1 | 100 | B-3 | 9.2 | PDB9 | 6.1 | D-1 | 1800 |
| Example 28 | H-28 | A-1 | 100 | B-4 | 9.0 | PDB1 | 5.0 | D-1 | 1800 |
| Example 29 | H-29 | A-1 | 100 | B-4 | 9.0 | PDB2 | 5.5 | D-1 | 1800 |
| Example 30 | H-30 | A-1 | 100 | B-4 | 9.0 | PDB3 | 6.1 | D-1 | 1800 |
| Example 31 | H-31 | A-1 | 100 | B-4 | 9.0 | PDB4 | 6.2 | D-1 | 1800 |
| Example 32 | H-32 | A-1 | 100 | B-4 | 9.0 | PDB5 | 6.0 | D-1 | 1800 |
| Example 33 | H-33 | A-1 | 100 | B-4 | 9.0 | PDB6 | 6.5 | D-1 | 1800 |
| Example 34 | H-34 | A-1 | 100 | B-4 | 9.0 | PDB7 | 7.0 | D-1 | 1800 |
| Example 35 | H-35 | A-1 | 100 | B-4 | 9.0 | PDB8 | 7.1 | D-1 | 1800 |
| Example 36 | H-36 | A-1 | 100 | B-4 | 9.0 | PDB9 | 6.1 | D-1 | 1800 |
| Example 37 | H-37 | A-2 | 100 | B-3 | 9.0 | PDB3 | 6.0 | D-1 | 1800 |
| Example 38 | H-38 | A-2 | 100 | B-3 | 9.0 | PDB7 | 7.0 | D-1 | 1800 |
| Example 39 | H-39 | A-3 | 100 | B-3 | 9.0 | PDB3 | 6.0 | D-1 | 1800 |
| Example 40 | H-40 | A-3 | 100 | B-3 | 9.0 | PDB7 | 7.0 | D-1 | 1800 |
| Comparative Example 1 | H-41 | A-1 | 100 | B-1 | 8.0 | PDB10 | 3.8 | D-1 | 1800 |
| Comparative Example 2 | H-42 | A-1 | 100 | B-2 | 9.0 | PDB10 | 3.8 | D-1 | 1800 |
| Comparative Example 3 | H-43 | A-1 | 100 | B-3 | 9.2 | PDB10 | 3.8 | D-1 | 1800 |
| Comparative Example 4 | H-44 | A-1 | 100 | B-4 | 9.0 | PDB10 | 3.8 | D-1 | 1800 |
| Comparative Example 5 | H-45 | A-1 | 100 | B-1 | 8.0 | PDB11 | 4.3 | D-1 | 1800 |
| Comparative Example 6 | H-46 | A-1 | 100 | B-2 | 9.0 | PDB11 | 4.3 | D-1 | 1800 |
| Comparative Example 7 | H-47 | A-1 | 100 | B-3 | 9.2 | PDB11 | 4.3 | D-1 | 1800 |
| Comparative Example 8 | H-48 | A-1 | 100 | B-4 | 9.0 | PDB11 | 4.3 | D-1 | 1800 |
| Comparative Example 9 | H-49 | A-1 | 100 | B-1 | 8.0 | PDB12 | 4.8 | D-1 | 1800 |
| Comparative Example 10 | H-50 | A-1 | 100 | B-2 | 9.0 | PDB12 | 4.8 | D-1 | 1800 |
| Comparative Example 11 | H-51 | A-1 | 100 | B-3 | 9.2 | PDB12 | 4.8 | D-1 | 1800 |
| Comparative Example 12 | H-52 | A-1 | 100 | B-4 | 9.0 | PDB12 | 4.8 | D-1 | 1800 |
| Comparative Example 13 | H-53 | A-1 | 100 | B-1 | 8.0 | PDB13 | 4.9 | D-1 | 1800 |
| Comparative Example 14 | H-54 | A-1 | 100 | B-2 | 9.0 | PDB13 | 4.9 | D-1 | 1800 |
| Comparative Example 15 | H-55 | A-1 | 100 | B-3 | 9.2 | PDB13 | 4.9 | D-1 | 1800 |
| Comparative Example 16 | H-56 | A-1 | 100 | B-4 | 9.0 | PDB13 | 4.9 | D-1 | 1800 |
| Comparative Example 17 | H-57 | A-1 | 100 | B-1 | 8.0 | PDB12 | 4.8 | D-1 | 1800 |

TABLE 1-continued

| Resist Composition | Polymer Type | Polymer Blend amount (part by mass) | Photoacid Generator Type | Photoacid Generator Blend amount (part by mass) | Photodegradable Base Type | Photodegradable Base Blend amount (part by mass) | Solvent Type | Solvent Blend amount (part by mass) |
|---|---|---|---|---|---|---|---|---|
| Comparative Example 18 | H-58 | A-1 | 100 | B-2 | 9.0 | PDB13 | 4.9 | D-1 | 1800 |
| Comparative Example 19 | H-59 | A-1 | 100 | B-3 | 9.2 | PDB12 | 4.8 | D-1 | 1800 |
| Comparative Example 20 | H-60 | A-1 | 100 | B-4 | 9.0 | PDB13 | 4.9 | D-1 | 1800 |
| Comparative Example 21 | H-61 | A-2 | 100 | B-3 | 9.0 | PDB12 | 4.8 | D-1 | 1800 |
| Comparative Example 22 | H-62 | A-3 | 100 | B-3 | 9.0 | PDB12 | 4.8 | D-1 | 1800 |

Each pKa of Photodegradable Base (PDB 1) to (PDB 13) and Photoacid Generators (B-1) to (B-4) used in Examples and Comparative Examples is as follows. PDB 1: 1.17, PDB 2: −3.57, PDB 3: −2.76, PDB 4: −2.76, PDB 5: 1.17, PDB 6: −3.57, PDB 7: −2.76, PDB 8: −2.76, PDB 9: −2.76, PDB 10: 1.17, PDB 11: −3.57, PDB 12: −2.76, PDB 13: −2.76. B-1: −3.57, B-2: −2.76, B-3: −2.76, B-4: −2.76.

<Evaluation>

Each of Radiation Sensitive Resist Compositions was spin-coated on a silicon wafer by a spin coater and then prebaked on a hot plate at 110° C. for 60 seconds to obtain a coating film having a thickness of 150 nm. Using a mask to obtain a line pattern of 90 nm, exposure is performed with an ArF excimer laser stepper, wavelength of 193 nm, and post-baking is performed at 110° C. for 90 seconds. Thereafter, development is performed for 60 seconds using a 2.38 mass % tetramethylammonium hydroxide aqueous solution, and then rinse is performed with pure water for 30 seconds to obtain a substrate on which a pattern is formed.

Values of sensitivity, resolution, focal depth and line edge roughness of Comparative Example 1 at this time are used as standards. Each performance of the sensitivity, resolution, focal depth and line edge roughness of Examples 1 to 36 and Comparative Examples 2 to 16 in comparison with the respective standards is evaluated with the following indices. A scanning electron microscope is used for measuring resist pattern length.

Excellent: Improvement of 10% or more is observed compared with Comparative Example 1.
Good: Improvement of 5% or more to less than 10% is observed compared with Comparative Example 1.
Bad: Improvement of less than 5% is observed compared with Comparative Example 1.

(Sensitivity)

Sensitivity is described as a minimum exposure dose for reproducing the line pattern of 90 nm. Sensitivity is better as the minimum exposure dose is smaller.

(Resolution)

Resolution indicates width (nm) of the line pattern that can be resolved by the minimum exposure dose for reproducing the line pattern of 90 nm, that is, limit resolution. Resolution is better as the value thereof is smaller.

(Focal Depth)

Focal Depth indicates an allowable range of focus that can reproduce the line pattern of 90 nm when focus position is moved up and down to perform the exposure with the minimum exposure dose for reproducing the line pattern of 90 nm in the mask, and then to perform post exposure bake (PEB) and development. Focal depth is better as the range of focus is larger because change of the pattern size with respect to change of the focal depth is small.

(Line Edge Roughness: LER)

In range of edge of 2.5 μm in the longitudinal direction of the line pattern of 90 nm obtained by the minimum exposure dose for reproducing the line pattern of 90 nm, distances from a reference line where there should be the edge are measured at 50 points to calculate standard deviation (σ), and then its triple value (3σ) is calculated as LER. LER is better as the value of LER is smaller because a uniform pattern edge with a small roughness is obtained.

TABLE 2

| | Sensitivity | Resolution | Focal Depth | Line Edge Roughness |
|---|---|---|---|---|
| Example 1 | Good | Excellent | Good | Excellent |
| Example 2 | Excellent | Good | Excellent | Good |
| Example 3 | Excellent | Good | Excellent | Excellent |
| Example 4 | Excellent | Excellent | Excellent | Excellent |
| Example 5 | Good | Excellent | Good | Excellent |
| Example 6 | Excellent | Good | Excellent | Good |
| Example 7 | Excellent | Good | Excellent | Excellent |
| Example 8 | Excellent | Excellent | Excellent | Excellent |
| Example 9 | Excellent | Good | Excellent | Excellent |
| Example 10 | Good | Excellent | Good | Excellent |
| Example 11 | Excellent | Good | Excellent | Good |
| Example 12 | Excellent | Good | Excellent | Excellent |
| Example 13 | Excellent | Excellent | Excellent | Excellent |
| Example 14 | Good | Excellent | Good | Excellent |
| Example 15 | Excellent | Good | Excellent | Good |
| Example 16 | Excellent | Good | Excellent | Excellent |
| Example 17 | Excellent | Excellent | Excellent | Excellent |
| Example 18 | Excellent | Good | Excellent | Excellent |
| Example 19 | Good | Excellent | Good | Excellent |
| Example 20 | Excellent | Good | Excellent | Good |
| Example 21 | Excellent | Excellent | Excellent | Excellent |
| Example 22 | Excellent | Excellent | Excellent | Excellent |
| Example 23 | Good | Excellent | Good | Excellent |
| Example 24 | Excellent | Good | Excellent | Good |
| Example 25 | Excellent | Excellent | Excellent | Excellent |
| Example 26 | Excellent | Excellent | Excellent | Excellent |
| Example 27 | Excellent | Excellent | Excellent | Excellent |
| Example 28 | Good | Excellent | Good | Excellent |
| Example 29 | Excellent | Good | Excellent | Good |
| Example 30 | Excellent | Excellent | Excellent | Excellent |
| Example 31 | Excellent | Excellent | Excellent | Excellent |
| Example 32 | Good | Excellent | Good | Excellent |
| Example 33 | Excellent | Good | Excellent | Good |
| Example 34 | Excellent | Excellent | Excellent | Excellent |
| Example 35 | Excellent | Excellent | Excellent | Excellent |
| Example 36 | Excellent | Excellent | Good | Excellent |
| Example 37 | Excellent | Excellent | Excellent | Excellent |
| Example 38 | Excellent | Excellent | Good | Excellent |
| Example 39 | Excellent | Excellent | Excellent | Excellent |
| Example 40 | Excellent | Excellent | Good | Excellent |

TABLE 2-continued

| | Sensitivity | Resolution | Focal Depth | Line Edge Roughness |
|---|---|---|---|---|
| Comparative Example 1 | — | — | — | — |
| Comparative Example 2 | Bad | Good | Bad | Good |
| Comparative Example 3 | Bad | Good | Good | Good |
| Comparative Example 4 | Bad | Good | Good | Good |
| Comparative Example 5 | Good | Bad | Good | Bad |
| Comparative Example 6 | Good | Bad | Good | Bad |
| Comparative Example 7 | Good | Bad | Good | Bad |
| Comparative Example 8 | Good | Bad | Good | Bad |
| Comparative Example 9 | Good | Bad | Good | Bad |
| Comparative Example 10 | Good | Bad | Good | Bad |
| Comparative Example 11 | Good | Bad | Good | Bad |
| Comparative Example 12 | Good | Bad | Good | Bad |
| Comparative Example 13 | Good | Bad | Good | Bad |
| Comparative Example 14 | Good | Bad | Good | Bad |
| Comparative Example 15 | Good | Bad | Good | Bad |
| Comparative Example 16 | Good | Bad | Good | Bad |
| Comparative Example 17 | Good | Bad | Good | Bad |
| Comparative Example 18 | Good | Bad | Good | Bad |
| Comparative Example 19 | Good | Bad | Good | Bad |
| Comparative Example 20 | Good | Bad | Good | Bad |
| Comparative Example 21 | Good | Bad | Good | Bad |
| Comparative Example 22 | Good | Bad | Good | Bad |

Examples 1 to 40 using Photodegradable Base (PDBs 1 to 9) containing the specific metal are excellent in the characteristics of the sensitivity, resolution, focal depth and LWR. On the other hand, Comparative Examples 1 to 20 using Photodegradable Base (PDBs 10 to 13) not containing the metal cause problems in the characteristics of the sensitivity, resolution, focal depth and LWR.

From the above results, it is found that the resist composition containing the metal-containing onium salt compound in one embodiment of the present invention as the photodegradable base has excellent sensitivity, resolution and focal depth in lithography, and has the effect of reducing the LWR in the fine pattern.

INDUSTRIAL APPLICABILITY

The resist composition according to one embodiment of the present invention increases the film absorption of the ionizing radiation such as the extreme ultraviolet (EUV) and the like, and the secondary electron generation efficiency, resulting that the generation of acid from the photoacid generator in the exposed portion can be improved. On the other hand, since undegraded metal-containing onium salt compound acts as the acid diffusion control agent in the unexposed portion, it is excellent in sensitivity, resolution and focal depth in lithography, and LER (line edge roughness) in the fine pattern can be reduced.

What is claimed is:

1. A metal-containing onium salt compound represented by the following Formula (1),

wherein in the above Formula (1):
each of $R^1$ and $R^2$ is independently an alkyl group having 1 to 20 carbon atoms or an aryl group having 5 to 20 carbon atoms, where a part or all of hydrogen atoms of the alkyl group and the aryl group may be substituted;
$Ar^1$ is an arylene group having 5 to 20 carbon atoms, where a part or all of hydrogen atoms of the arylene group may be substituted;
the alkyl group may contain a hetero atom-containing group instead of at least one methylene group thereof, and the aryl group and the arylene group may contain a hetero atom instead of at least one carbon atom in ring structure thereof;
M is;
Y is any one selected from the group consisting of an iodine atom, a sulfur atom, a selenium atom and a tellurium atom;
n is 1 when Y is the iodine atom, and n is 2 when Y is any one selected from the group consisting of the sulfur atom, the selenium atom and the tellurium atom;
any two or more of $Ar^1$ and two $R^2$ may be bonded to each other to form a ring structure with Y bonded thereto, and the ring structure may contain a hetero atom; and
$X^-$ is an anion.

2. The metal-containing onium salt compound according to claim 1, wherein the metal-containing onium salt compound is represented by the following Formula (2) or (3),

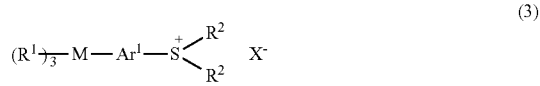

where each of $R^1$, $R^2$, M, $Ar^1$ and $X^-$ in the above Formulae (2) and (3) is the same as each of $R^1$, $R^2$, M, $Ar^1$ and $X^-$ in the above Formula (1).

3. A photodegradable base comprising the metal-containing onium salt according to claim 1.

4. A resist composition comprising the photodegradable base according to claim 3.

5. The resist composition according to claim 4, further comprising:
a photoacid generator; and
an acid-reactive compound.

6. The resist composition according to claim 5, wherein the acid-reactive compound is at least one selected from the group consisting of: a compound having a protecting group to be deprotected by acid; a compound having a polymerizable group to be polymerized by acid; and a crosslinking agent exerting a crosslinking action by acid.

7. A method for manufacturing a device comprising:
forming a resist film on a substrate using the resist composition according to claim 4;
exposing the resist film; and
obtaining a resist pattern by developing an exposed resist film.

8. The method according to claim 7, wherein the exposing the resist film is carried out using electron beam or extreme ultraviolet.

9. The metal-containing onium salt compound according to claim 1, wherein Y is any one selected from the group consisting of the iodine atom, the sulfur atom and the tellurium atom.

10. The metal-containing onium salt compound according to claim 9, wherein a cation of the metal-containing onium salt compound is a monocation.

* * * * *

UNITED STATES PATENT AND TRADEMARK OFFICE
CERTIFICATE OF CORRECTION

PATENT NO. : 11,347,147 B2
APPLICATION NO. : 16/344093
DATED : May 31, 2022
INVENTOR(S) : Michiya Naito et al.

It is certified that error appears in the above-identified patent and that said Letters Patent is hereby corrected as shown below:

In the Claims

Claim 1, Line 22, please change "M is;" to "M is Sn;"

Signed and Sealed this
Second Day of August, 2022

Katherine Kelly Vidal
*Director of the United States Patent and Trademark Office*